(12) United States Patent
Monteiro

(10) Patent No.: US 10,369,358 B2
(45) Date of Patent: Aug. 6, 2019

(54) METHOD AND MEANS TO IMPROVE THE EFFECTS OF ELECTRICAL CELL AND NEURON STIMULATION WITH RANDOM STIMULATION IN BOTH LOCATION AND TIME

(71) Applicant: Sergio Lara Pereira Monteiro, Los Angeles, CA (US)

(72) Inventor: Sergio Lara Pereira Monteiro, Los Angeles, CA (US)

( * ) Notice: Subject to any disclaimer, the term of this patent is extended or adjusted under 35 U.S.C. 154(b) by 123 days.

(21) Appl. No.: 15/275,304

(22) Filed: Sep. 23, 2016

(65) Prior Publication Data

US 2017/0007828 A1    Jan. 12, 2017

Related U.S. Application Data

(63) Continuation-in-part of application No. 14/741,136, filed on Jun. 16, 2015, now abandoned, which is a
(Continued)

(51) Int. Cl.
| | | |
|---|---|---|
| *A61N 1/08* | (2006.01) | |
| *A61N 1/36* | (2006.01) | |
| *A61N 1/02* | (2006.01) | |
| *A61N 1/05* | (2006.01) | |
| *A61N 1/04* | (2006.01) | |

(Continued)

(52) U.S. Cl.
CPC ............... *A61N 1/08* (2013.01); *A61B 34/70* (2016.02); *A61N 1/025* (2013.01); *A61N 1/0456* (2013.01); *A61N 1/0529* (2013.01); *A61N 1/0534* (2013.01); *A61N 1/0539* (2013.01); *A61N 1/0551* (2013.01); *A61N 1/0587* (2013.01); *A61N 1/3606* (2013.01); *A61N 1/36014* (2013.01); *A61N 1/36071* (2013.01); *A61N 1/3686* (2013.01); *A61N 1/36103* (2013.01); *A61N 1/36182* (2013.01); *A61N 1/36185* (2013.01); *A61N 1/057* (2013.01); *A61N 1/3684* (2013.01); *A61N 1/375* (2013.01)

(58) Field of Classification Search
None
See application file for complete search history.

(56) References Cited

U.S. PATENT DOCUMENTS

| | | | | |
|---|---|---|---|---|
| 7,146,219 B2 * | 12/2006 | Sieracki | ................... | A61N 1/08 607/46 |
| 7,848,802 B2 * | 12/2010 | Goetz | ................ | A61N 1/37247 607/2 |
| 7,957,814 B2 * | 6/2011 | Goetz | ................ | A61N 1/36071 607/45 |

* cited by examiner

*Primary Examiner* — Brian T Gedeon

(57) ABSTRACT

An electric stimulator for brain, heart, skin and internal organs in animals and plants where the electrodes are distributed on a supporting structure. The supporting structure may be adapted for brain, heart, skin or other internal organs, as for DBS, heart pacemaker, TENS, etc. The invention discloses a plurality of electrodes at the surface of the supporting structure, from which electrically stimulating currents can be injected into the organism. Turning off an electrode while turning on another electrode has the effect of moving the stimulation within the body of the organism from one point to another point, with the same effect but with less spent energy than physically moving the whole electrode support. We call this electrode shifting. Rotational and translational electrode shifting are possible. The invention also discloses random changes of the electrode shifting, and random changes of the stimulation time and of the stimulation duration.

13 Claims, 17 Drawing Sheets

Related U.S. Application Data continuation of application No. 14/150,767, filed on Jan. 9, 2014, now Pat. No. 9,089,687, which is a continuation of application No. 13/117,132, filed on May 26, 2011, now Pat. No. 8,670,837.

(60) Provisional application No. 61/396,334, filed on May 26, 2010, provisional application No. 61/340,920, filed on Mar. 24, 2010.

(51) Int. Cl.
*A61N 1/368* (2006.01)
*A61B 34/00* (2016.01)
*A61N 1/375* (2006.01)

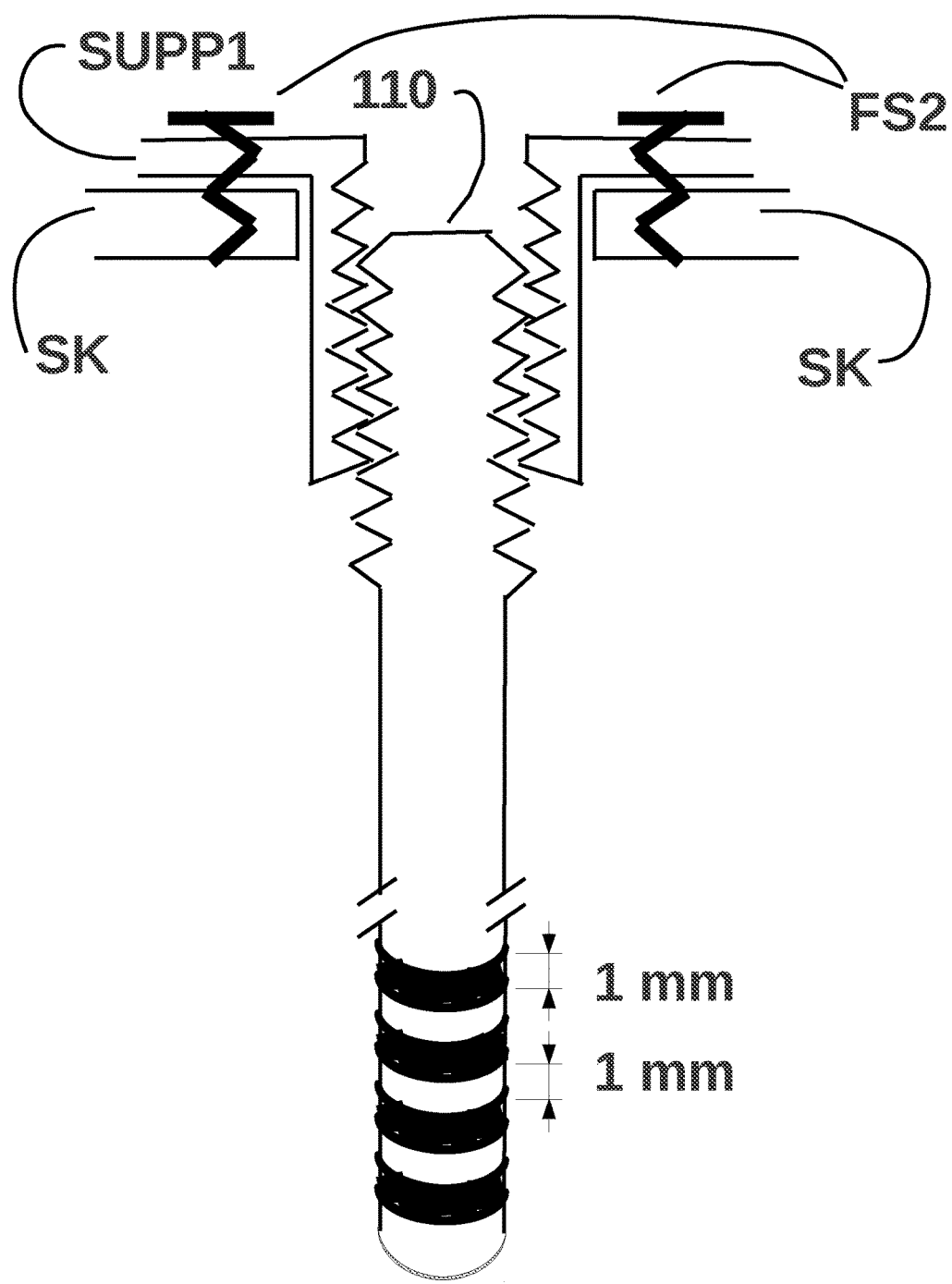
Figure FIG1

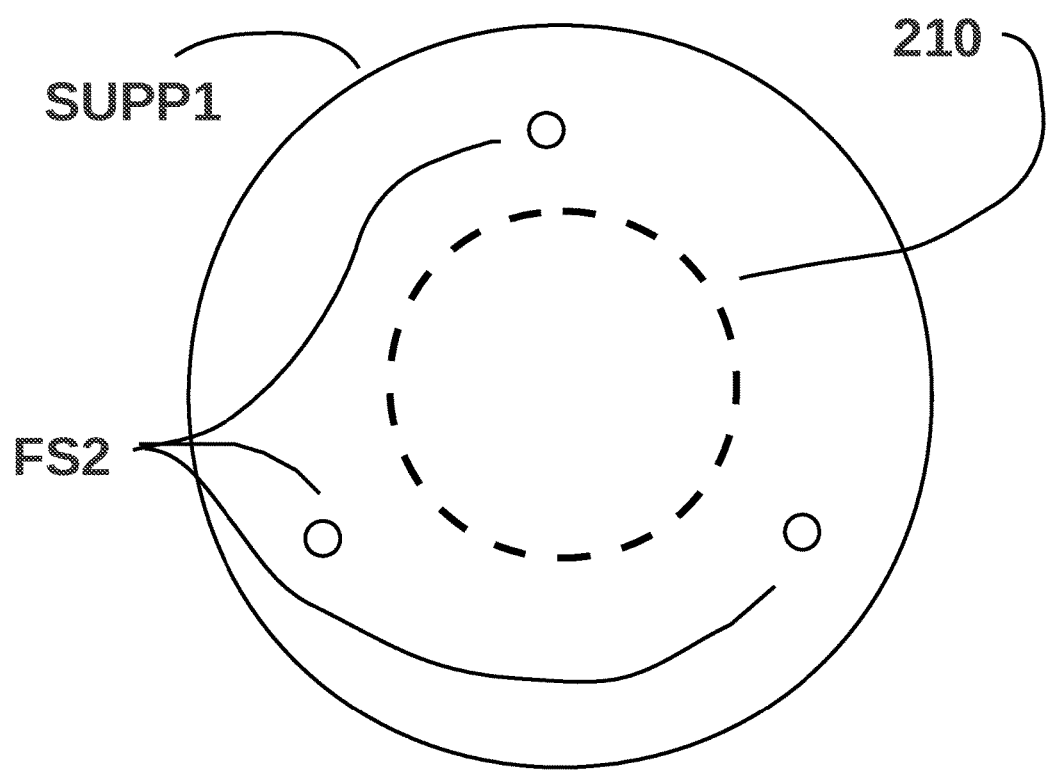
Figure FIG2

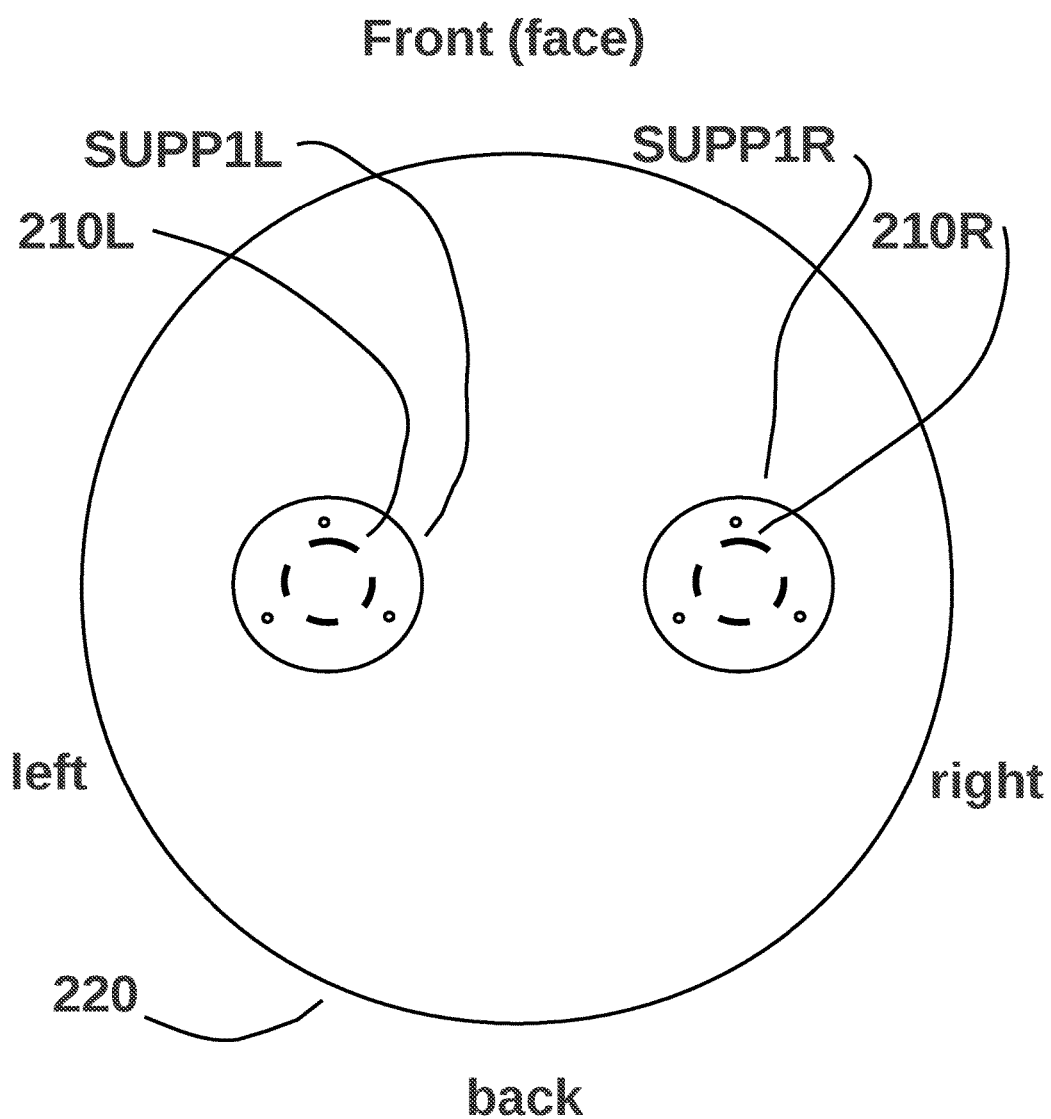

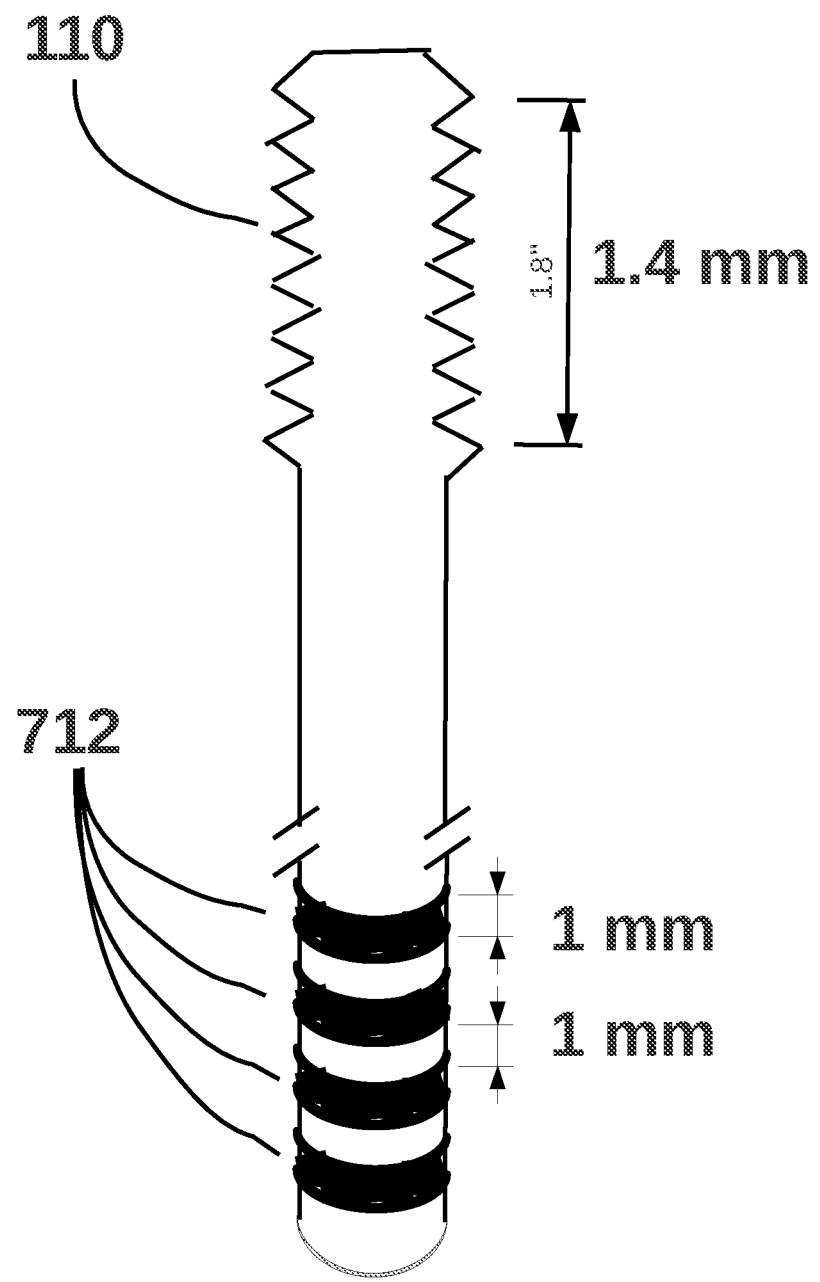

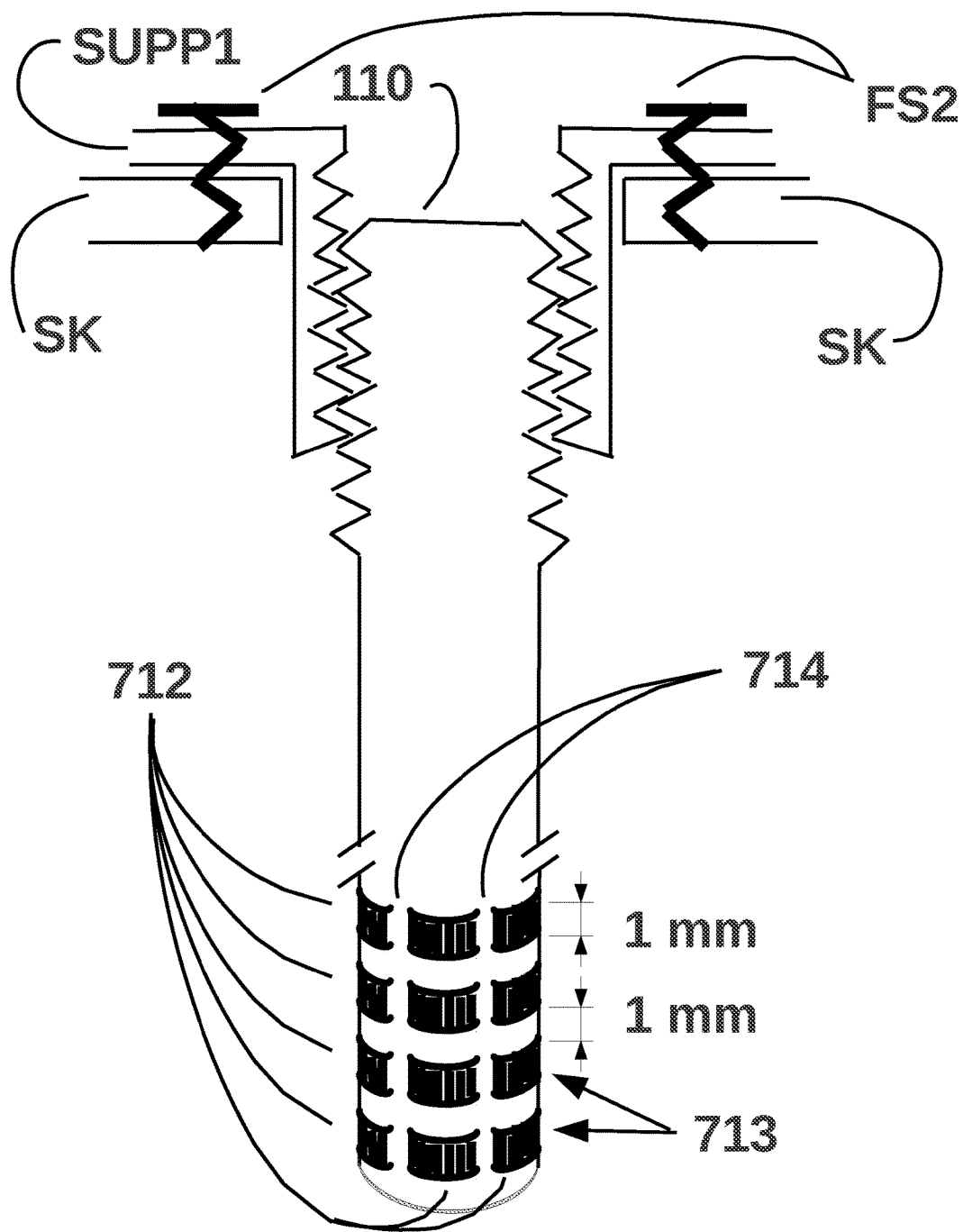
Figure FIG4

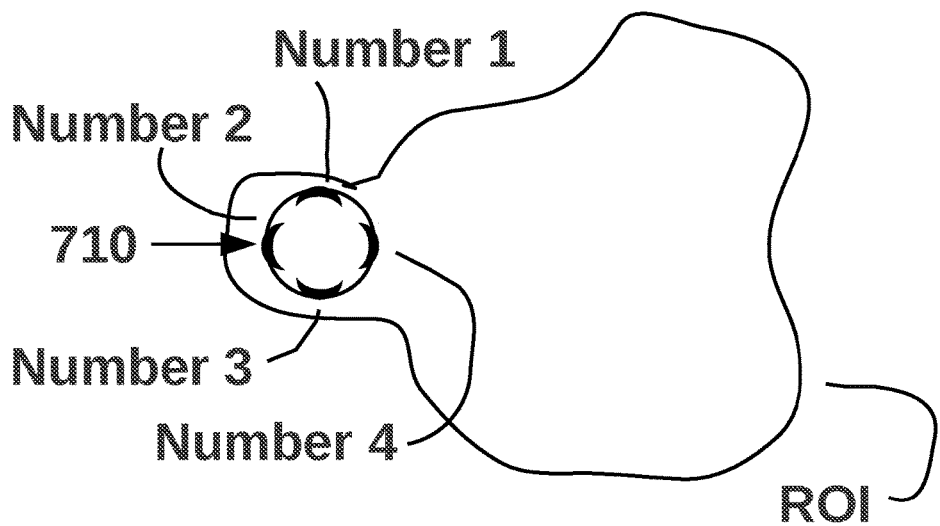
Figure FIG5a
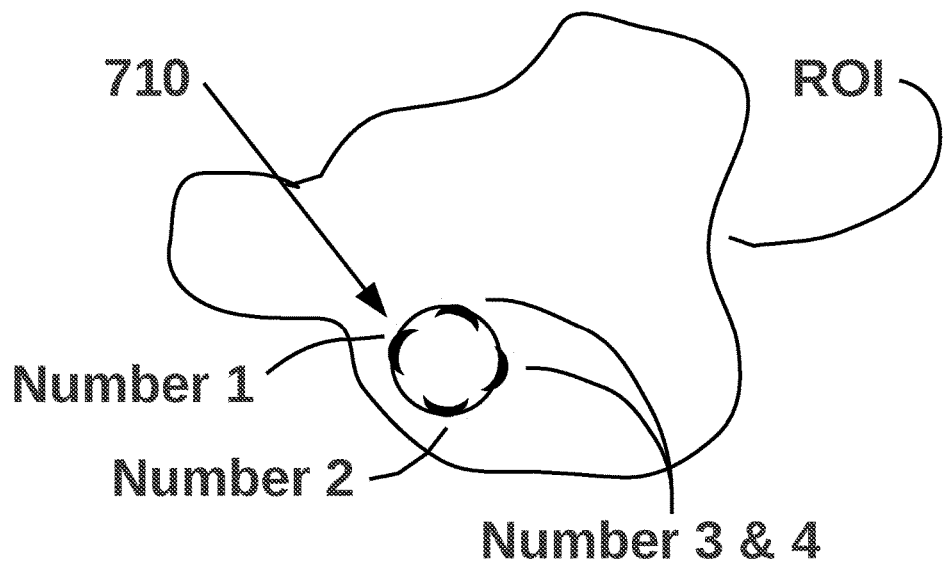
Figure FIG5b

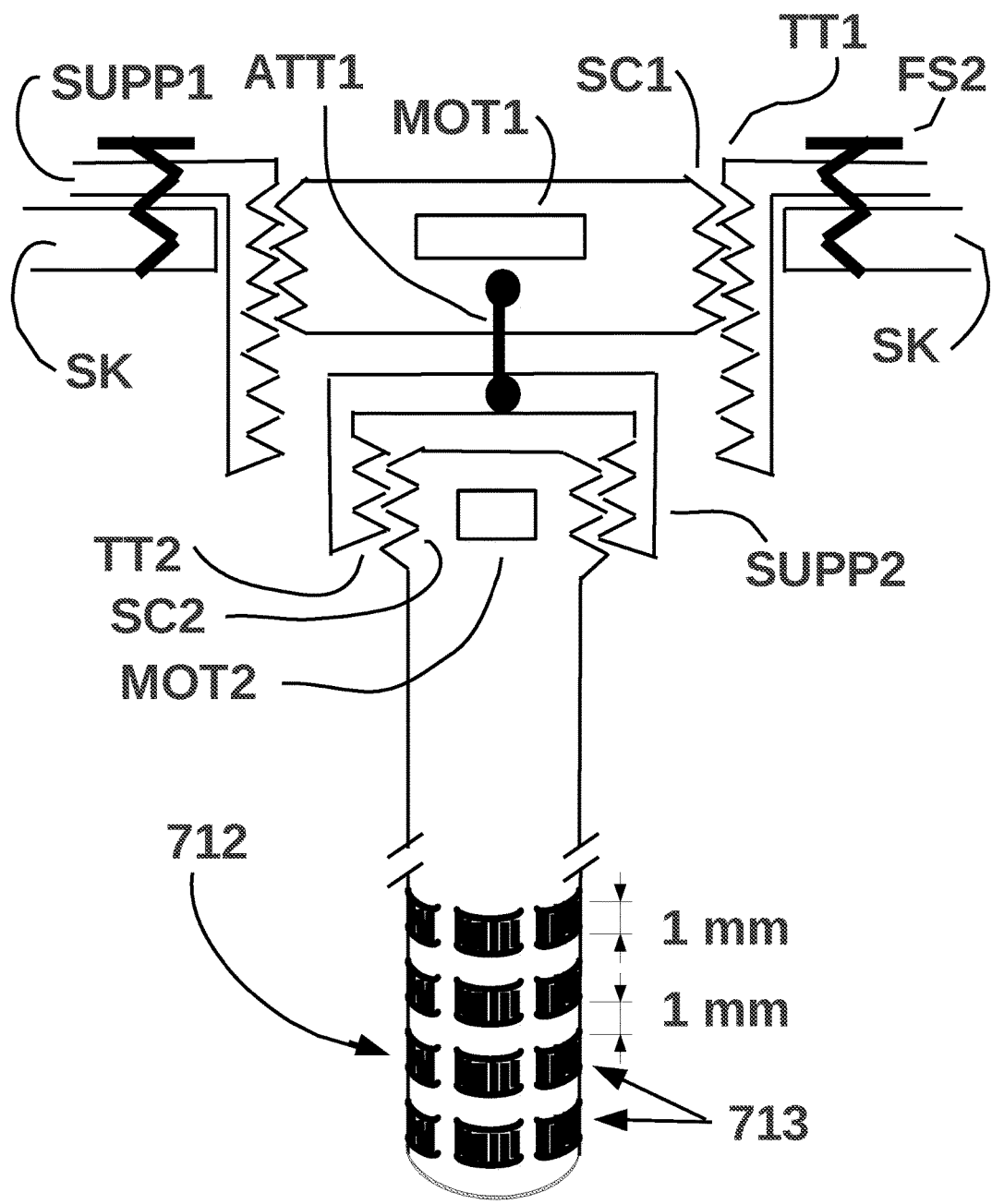

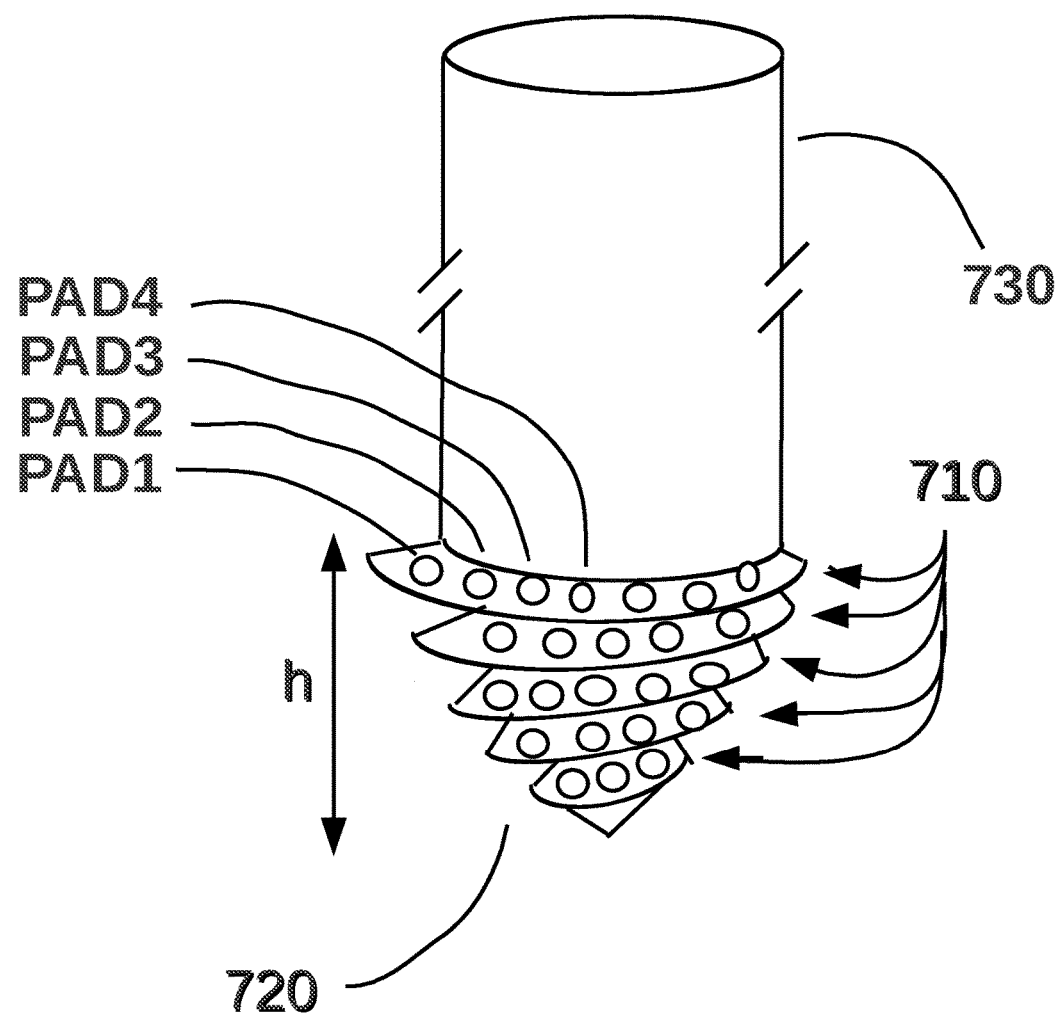

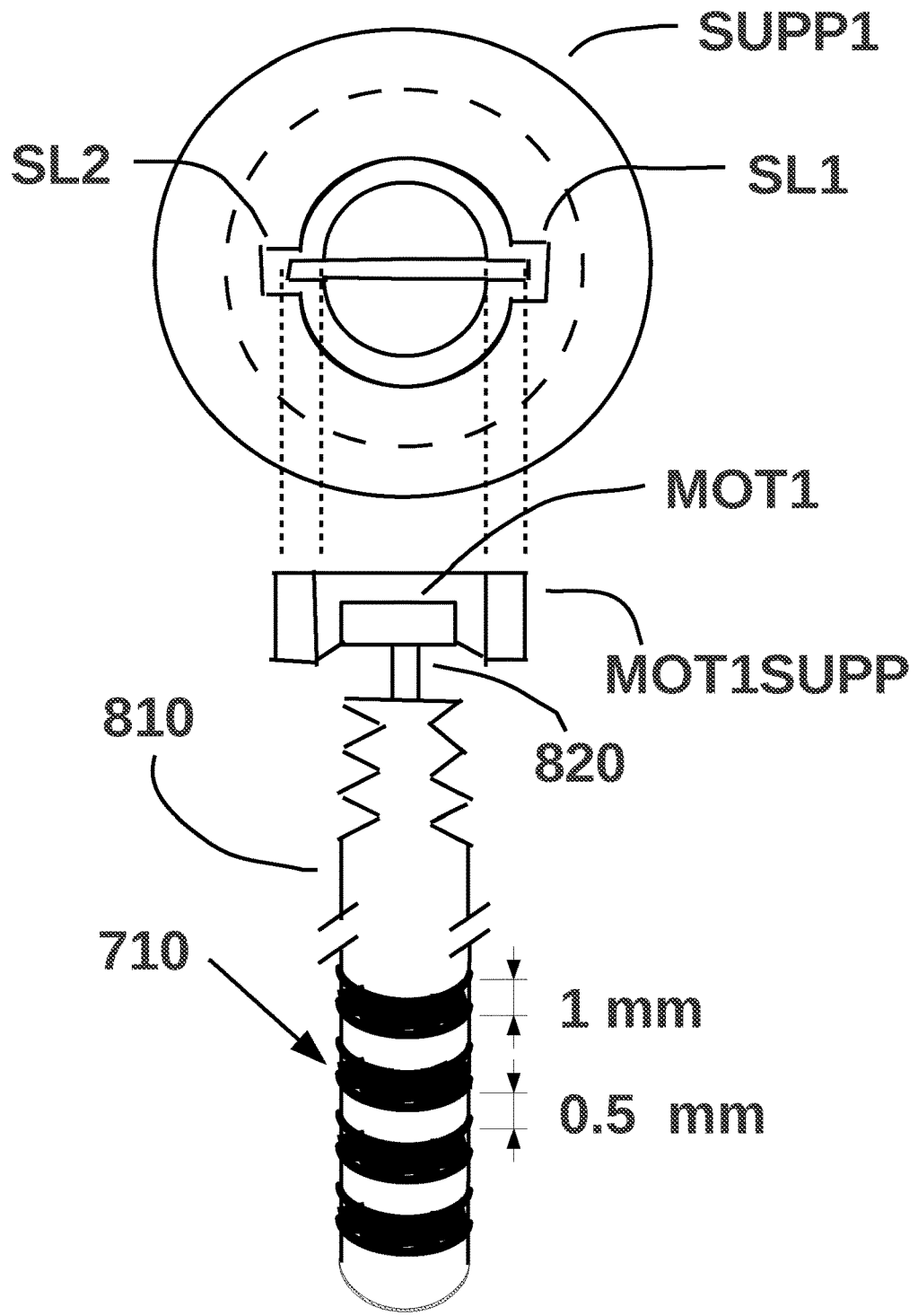

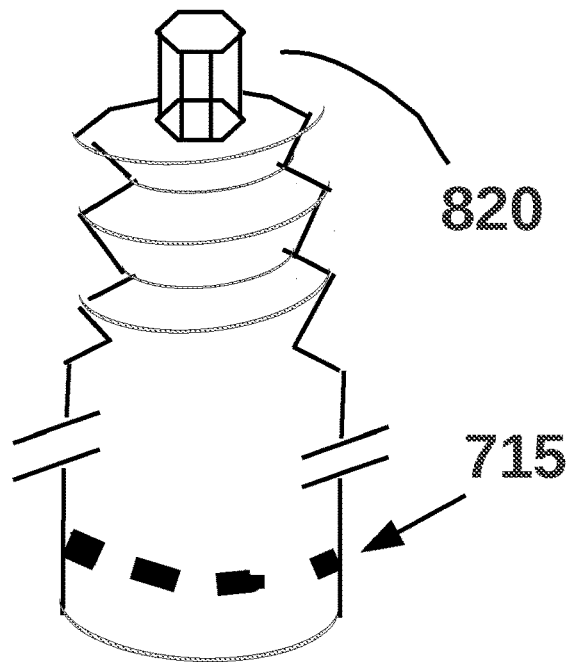
Figure FIG8b
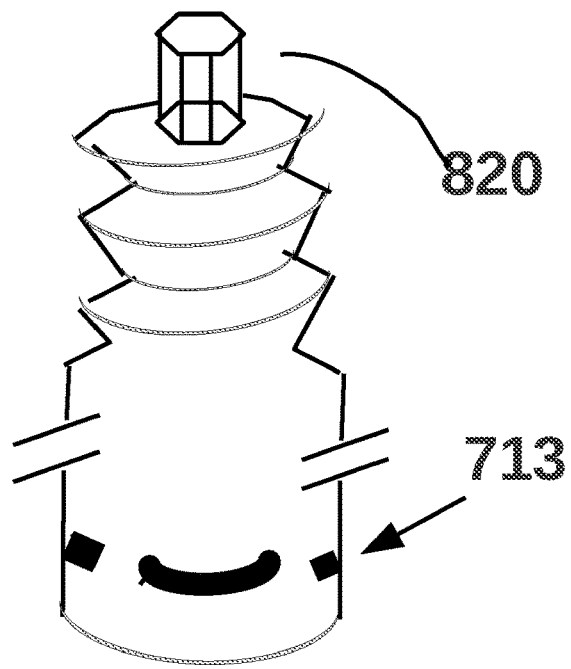
Figure FIG8a

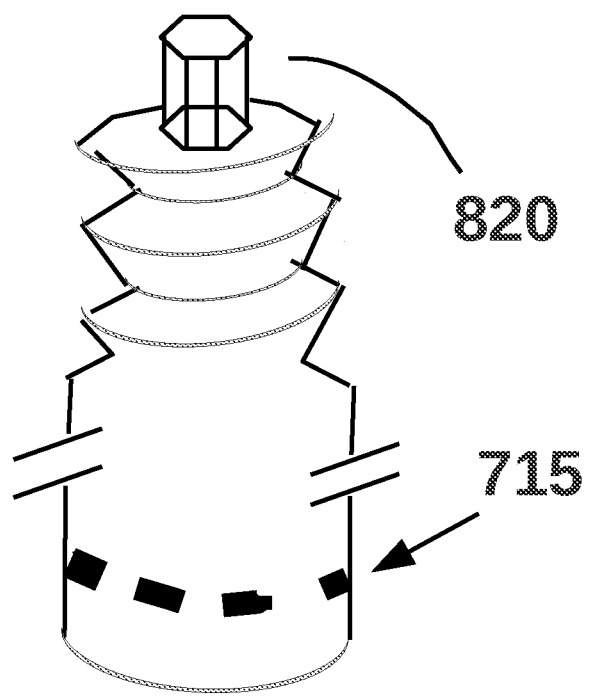
Figure FIG8c

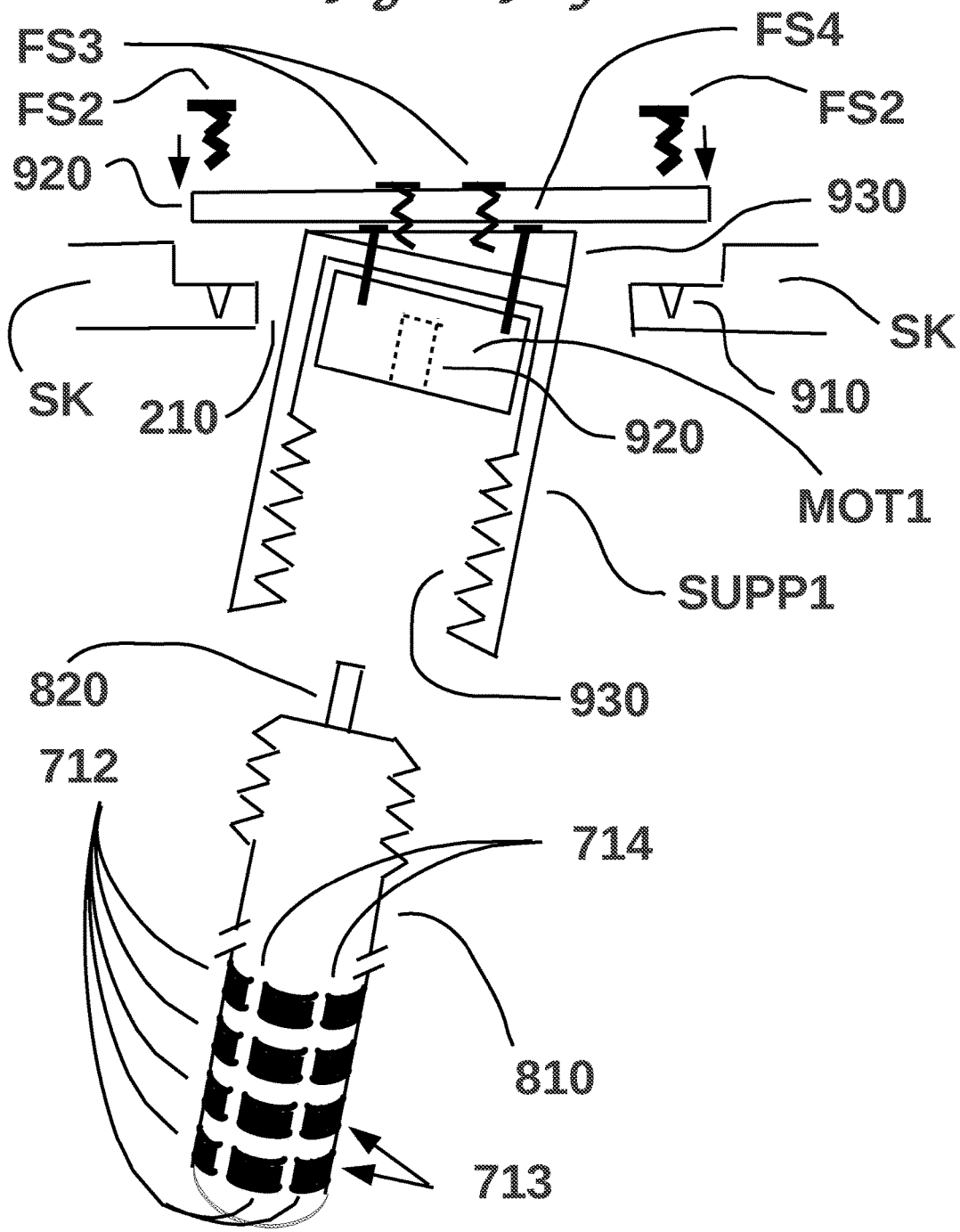

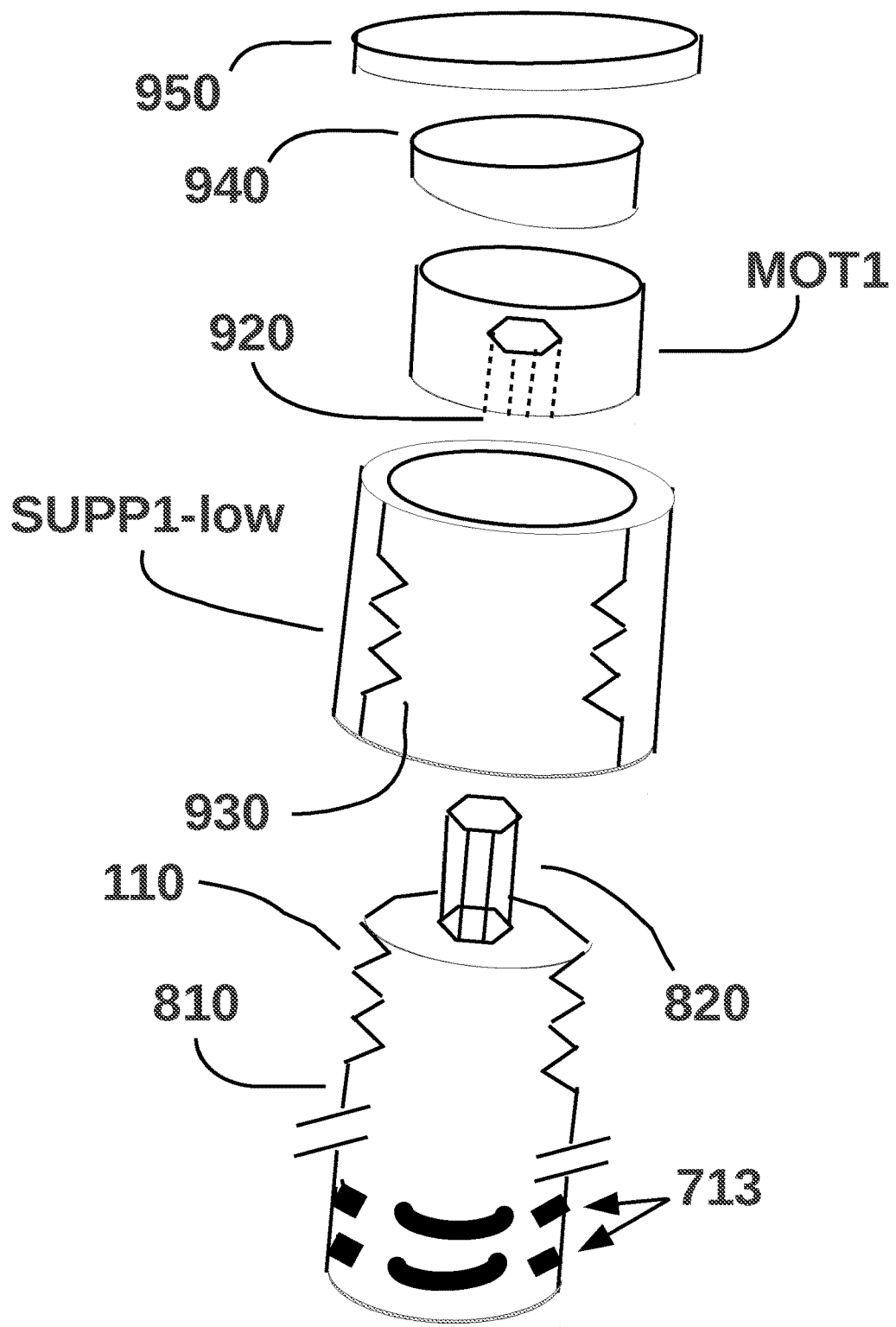

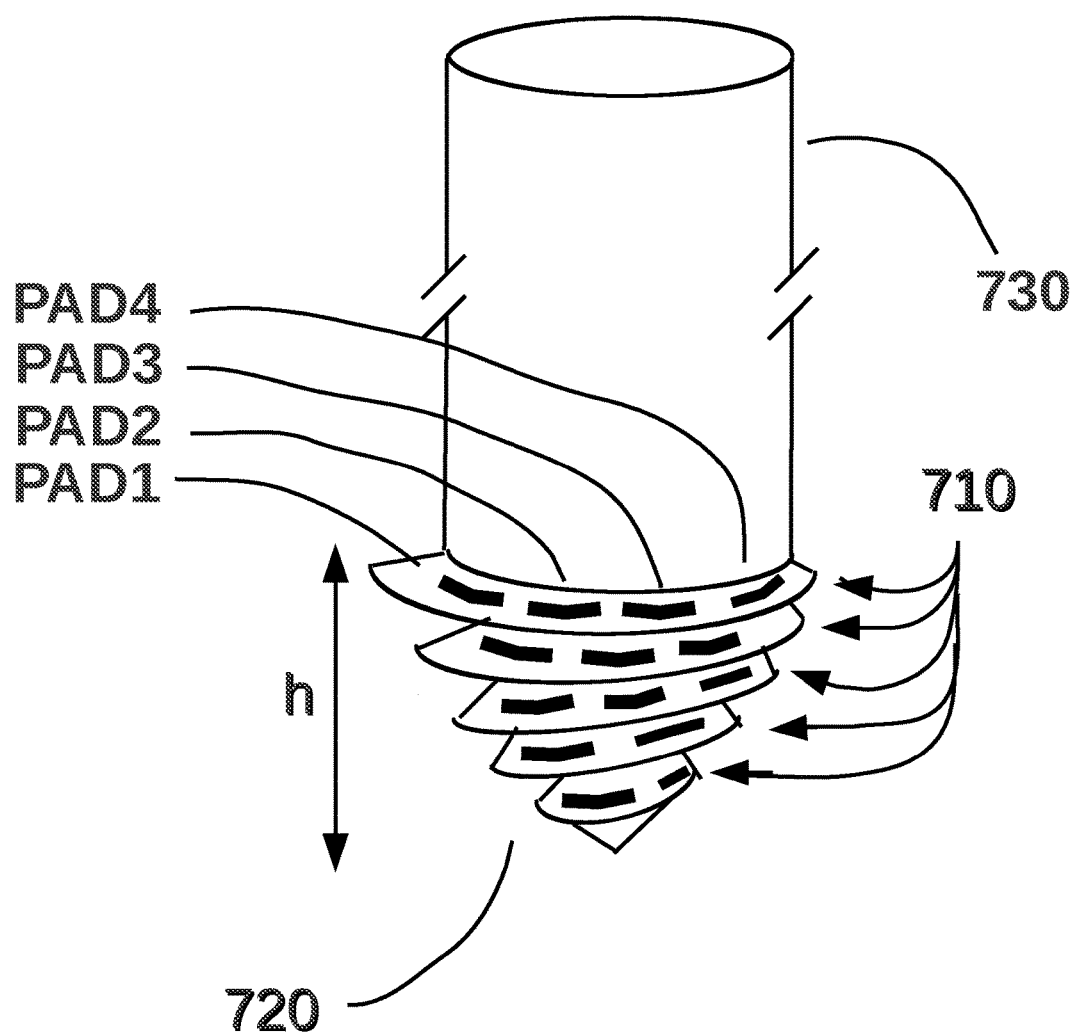

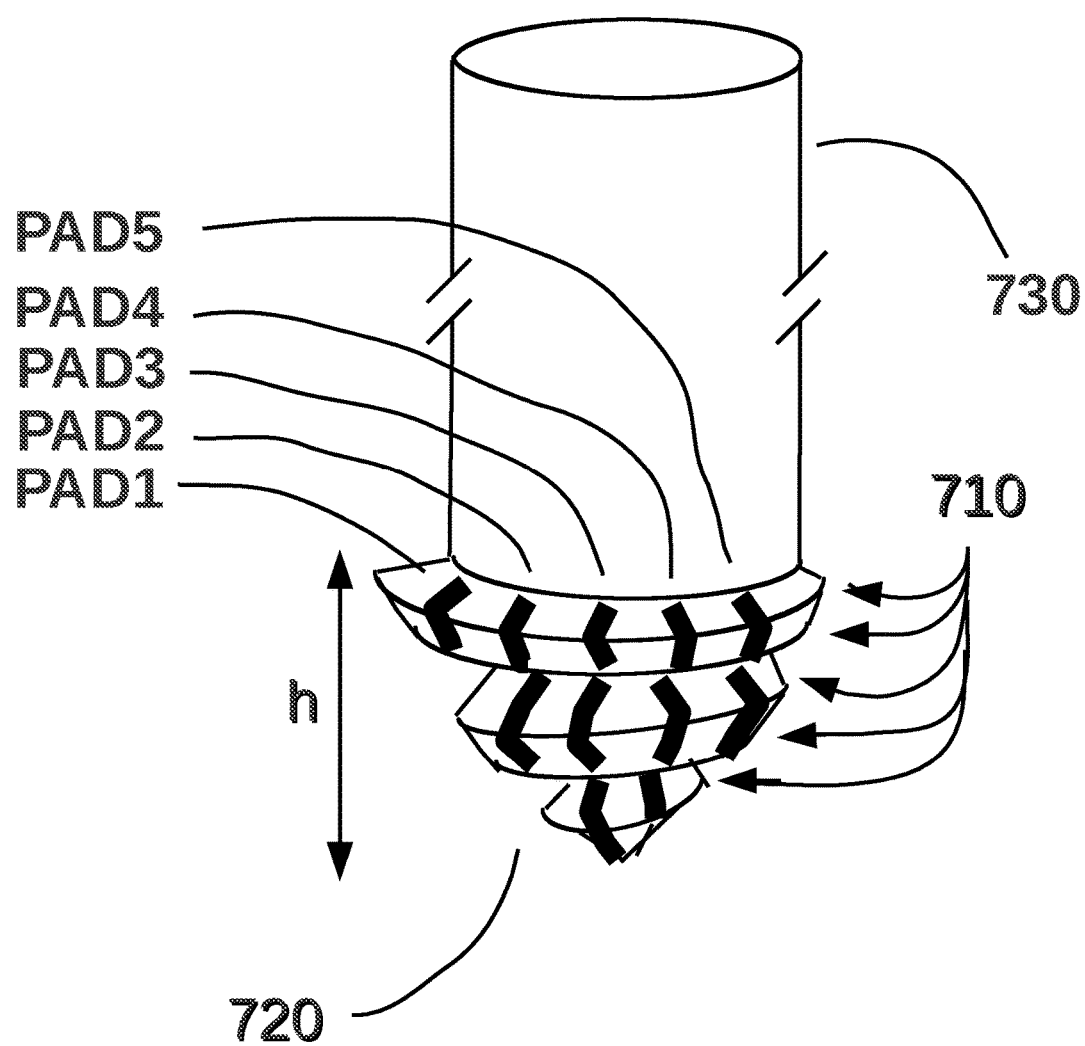
Figure FIG11b

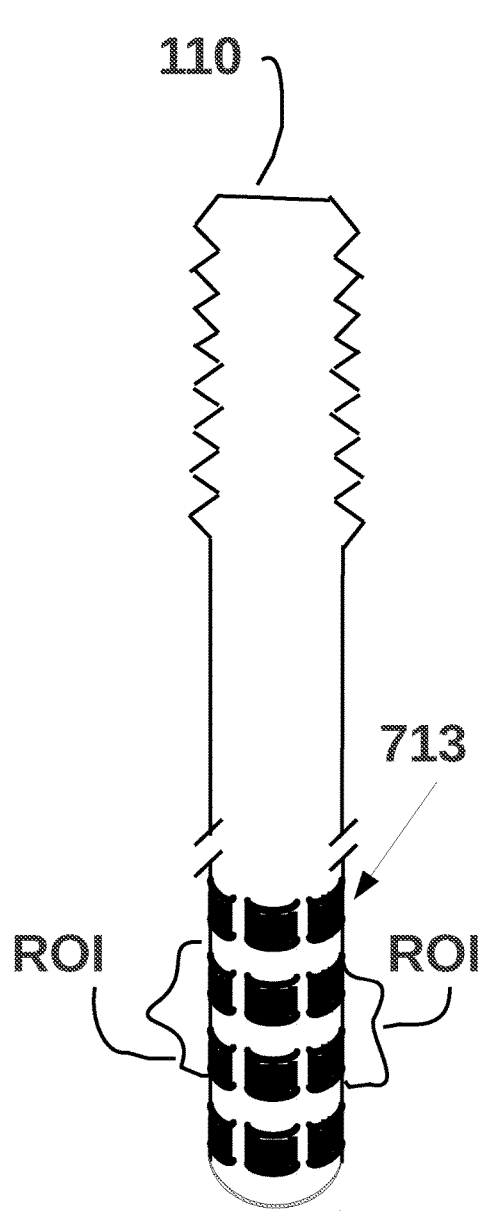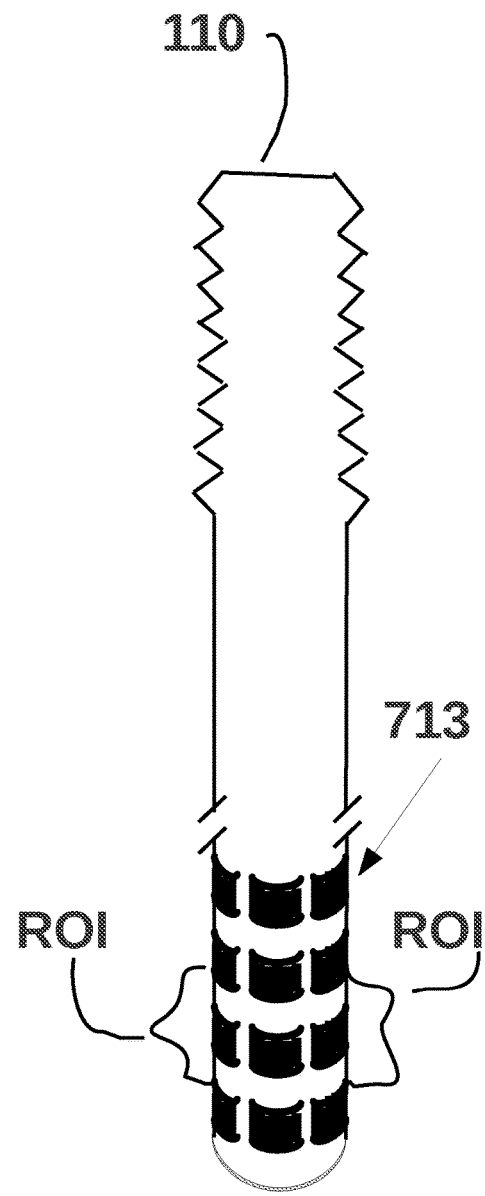

METHOD AND MEANS TO IMPROVE THE EFFECTS OF ELECTRICAL CELL AND NEURON STIMULATION WITH RANDOM STIMULATION IN BOTH LOCATION AND TIME

CROSS-REFERENCE TO RELATED APPLICATIONS

This application is a continuation in part of U.S. patent application Ser. No. 14/741,136, filing date 2015 Jun. 16, title "Method and means to adjust the positioning of stimulating neural and muscular electrode", now abandoned, which is a continuation of U.S. patent application Ser. No. 14/150,767, filing date 2014 Jan. 9, title "Device and means for adjusting the position of DBS brain and other neural and muscular implants", publication number US 2014-0222018 A1, publication date 2014 Aug. 7, now U.S. Pat. No. 9,089,687, issued on 2015 Jul. 28, which is a continuation of U.S. patent application Ser. No. 13/117,132, filing date 2011 May 26, title "Method and means to adjust the positioning of stimulating neural and muscular electrode, published US-2012-0029590 A1 on 2012 Feb. 2, now U.S. Pat. No. 8,670,837, issued on 2014 Mar. 11.

This application claims priority to U.S. PPA application No. 61/396,334, filing date 2010 May 26 "Method and means to adjust the positioning of stimulating neural and muscular electrode" and U.S. PPA application No. 61/340, 920, filing date 2010 Mar. 24. This patent application is related to U.S. PPA "Method and means to address and make use of multiple electrodes for measurements and electrical stimulation of neurons and other cells including brain and heart" by Chong Il Lee and Sergio Monteiro, application No. 61/340,920 of Mar. 24, 2010, RPA "Method and means for connecting and controlling a large number of contacts for electrical cell stimulation in living organisms" by Chong Il Lee and Sergio Monteiro, application Ser. No. 12/586,763, of Sep. 28, 2009, RPA "Method and means for connecting a large number of electrodes to a measuring device" by Chong Il Lee and Sergio Monteiro, application Ser. No. 12/586,562, of Sep. 24, 2009, which are included as references in their entirety.

FEDERALLY SPONSORED RESEARCH

Not applicable.

SEQUENCE LISTING OR PROGRAM

Not applicable.

BACKGROUND OF THE INVENTION

Field of Invention

This invention relates to cellular electrical stimulation in general, for animals, including humans, and neuronal and muscular electrical stimulation in particular, for brain, spinal cord, peripheral nerves, and muscles, as heart, organs and artificial limbs.

Discussion of Prior Art

It is well established that nerves work as a electrical conductor, neural information being simply electrical train of pulses—short burst of pulses repeated at short time intervals, potentially followed by a longer pause. Measurements on animals have shown that the brain works the same way, and in the few cases in which measurements have been made in humans, it has been confirmed that *H. sapiens* brain is also an electric machinery. The brain acts also as a network creator using synaptic generation and strengthening.

It follows that control of the electrical path of neurons in the brain, and flow of electrical current through its cells can potentially affect the brain activity, whether it be related to motor control, to emotion arousal or just a thought pattern. Among the clinical possibilities, correcting unwanted motion of limbs has been the most successful so far, and among these, control of Parkinson's Disease is a case. Parkinson's Disease control is not the only one, some other similar motor control being very successful too, as epilepsy and essential tremor. Other cases are now under evaluation, as depression and eating disorders, to mention just two examples. Electrical stimulation is also used to control pain, as in TENS devices, to control incontinency and potentially any other neuronal malfunction. And naturally that electrical stimulators are also used to adjust the heart beating with the pacemaker, which is one of the oldest application of electrical stimulation.

As an exemplary case we will take the DBS (Deep Brain Stimulation) for Parkinson's Disease control, which is one of the most successful corrective electrical stimulators for motion disorders today, with several thousand surgeries performed yearly. The success rate is nevertheless less than what could be. Some of the failures are due to side effects, which may well be a consequence of incorrectly placed stimulators, as acknowledged by many neurosurgeons, including in this case stimulators placed other than the exact center of the target area. The reader should keep in mind that the word "area" in brain means what is normally called a volume; it happens that the neurons that participate together for a particular function are generally connected on a network that is mostly flat (2-D), with little depth ($3^{rd}$ dimension), which is the origin of the word usage. Ultimately this word usage is adopted even when a particular "area" happens to be actually volumetric (that is, having a non-negligible $3^{rd}$ dimension). Indeed, it is very difficult for the neurosurgeon to place the stimulating electrode in the correct place, deep inside the brain and not even open to visual inspection. Current art, for example, the stimulating electrode manufactured by Medtronic (REF_Meditronic_nd), attempts to adjust the final stimulating position offering 4 ring-like stimulating elements, which are at the end of a wand, called "lead" by Medtronic (which we call picafina), each of which can be independently chosen as the stimulating element. These electrode stimulating elements, also called pads, can be controlled by an electronics controlling unit, which is configured to change the voltage and/or current at each electrode independently and all other necessary parameters as required by the medical use of the device. The rings are approximately 1 mm in width and separated by 1 mm too. Consequently, after insertion of the picafina in the patient's brain, it is possible to chose the stimulating site with the picafina in the same position, just connecting one ring or another ring to the electrical pulse circuit, while disconnecting the others, or to choose two rings, or many other possible combinations of rings. This final stimulating positioning adjustment is made after the surgery, to compensate for the expected inaccuracies of initial position of the picafina with respect to the desired placement in the brain. Stimulating ring selection can be also needed to compensate for later possible motion of the picafina with respect to the brain. Unfortunately, the picafina must be of small size in order to minimize injure to the brain tissue, which in turn precludes many wirings running through it, this being one of the reasons for the current devices having so few stimulating pads (or rings, or electrodes) which offer so few options for the origin of the stimulating pulses. Indeed, many neurosurgeons would like to have more options, more electrical pads to choose as initiation points for the electrical stimulation, but a solution for this problem was never found. One possible solution is disclosed in patents applied by some of us (INV1, INV2, INV3, INV4, INV5), but alternative solutions exist too. Our invention offers an improvement on this positioning of the stimulating electrodes, one improvement that may, at first sight, be equivalent to the physical displacement of the electrodes but in reality has more meat to it. This patent application discloses an improved stimulation pattern even using the existing fixed position stimulators while offering better clinical results according to some of the theories of brain working.

It is worth to point out that the prior art for DBS at the present moment is capable of initiate an electrical stimulation from any of the four rings, therefore offering a small (1 mm.) adjustment on the stimulation site, but it is not capable of offering adjustment on the stimulation site from the position where one of the ring is to another site where the insulator spacer is. If the ideal position of the stimulator happens to be where one of the separators are, either one of the two adjacent rings have to be selected, of both of them, but no more precise than this. Neither can prior art cause the stimulation to be along one direction only, though the authors are aware of one lead manufactured by Medtronic which sports a small number of isolated pads, which are not circular around the lead but more-or-less rectangular on the surface of the lead.

A similar problem is encountered by heart pacemakers. A pacemaker have to deliver electrical pulses to some particular point in or near the heart. Typically the delivery point is nowadays in the inner wall of the heart, but this is not necessarily so, some pacemakers being attached to the external wall of the heart too. There are malfunctions that are better treated with a dual electrode, and more than two electrodes may become common in the future. Some of these electrodes are inserted via a vein accessed near the neck into the inner wall of the atrium, or upper heart chamber, where the delivering electrode is screwed in the inner wall of the atrium for spatial stability and consistency of electrical delivery point. In current art devices, the tip of the flexible device is made of some electrically conductive material, which is connected by wires to a battery/electronic circuits, which are located elsewhere in the patient, usually the upper chest. Old art has the disadvantage that the electrical pulse is injected over the whole, or at least most of the volume of the attachment. This has the disadvantage that the pulse is injected over too large an area into the heart muscle to be able to control its propagation time, which is needed for a proper, sequential contraction of the heart muscle, needed for optimal pumping. If the electrical pulse is not injected correctly, then the heart pumping is not sequentially squeezing the blood forward, as needed, causing a non-optimal pumping.

Regarding the position, it is not necessary to attach the electrode to the atrium, and our invention should not be limited to this case. In this case the pacemaking pulse is delivered symmetrically around the screw, 360 degrees around it, and it is delivered by all the metallic (or conductive) part of the tip of the device. Yet, such symmetrical delivery is not desirable, because the normal, natural electrical pulse is known to travel through the heart along certain paths with specific speeds and delay times, starting from the sinus, these speeds and delays being a function of the electrical characteristics of the heart muscle, known in electrical engineering as resistance, capacitance, inductance, etc. Normally the pulse initiates from a nerve that delivers it on the coronary sinus, and from there the electrical pulse propagates with speeds that depend on the tissue properties along each direction, which is a much studied problem. This point of delivery is a problem that has not yet been solved, in spite of it being a known source of problems with the pacemaking pulse. Indeed, if the electrical pulse from the pacemaker is delivered in the wrong place then the heart will not beat correctly, because the contraction, which must happen in a particular sequence will not be correct. A good example of the problem is the analogy with a milkman, who must start squeezing the teat near the udder, with his pointing finger (which is usually the one closer to the udder), then the middle finger, then the annular finger, then the small finger by last, if the milk is to be extracted from the utter through the teat. If he reverts the order, or change the other in any way, either no milk at all, or at most less milk will be squeezed from the caw. The pathways for the electrical pulses that originate at the sinus node are well known and it is well known that replication of the natural electrical pulse would be ideal, but an ideal that has eluded the devices in current use. Ideally the heart surgeon would be able to precisely control the depth on the heart wall and direction of delivery of the electrical pulse, as opposed of the voltage only, which is the only controllable value in current art, which also delivers the pulse on all directions, which is not ideal either.

Objects and Advantages

One of the objects and advantages of this invention is to forestall the formation of newly created Ramón y Cajal networks (also known as Hebbian networks) and/or loops by the artificial stimulation, because these Ramón y Cajal networks and/or loops may become new sources of involuntary movements. Though the inventor firmly believes that the artificial stimulation may give origin to new Ramón y Cajal networks and/or loops, there is no need for Ramón y Cajal networks and/or loops to be the cause of deleterious consequences of the artificial stimulation for the invention to work as predicted, because as any other mechanism associated with repetitive behavior learning, including non-specific Skiner-type behavior modification, could be the cause and the final result would be the same (ref Robert Miller 1991) This possibility is also supported by Enrico Opri et al.

Another of the advantages of this invention is to adjust the position of the brain stimulation to the best place to cause optimal results for the patient.

Another advantage of this invention is the decrease of side effects due to mis-positioning of the stimulating picafina.

Another advantage of this invention is the adjustment of the depth of penetration of the electrode screwed into the inner wall of the heart (atrium or otherwise), in order to deliver the pacemaking pulse at a precise depth and on a particular direction, adjusted to the particular patient's case, in order to provide a better pulse timing and delay, to ultimately create a better possible contraction sequence of the heart muscle therefore improving the heart pumping capability.

Still another advantage is the possibility of controlling which said tips are on or off without using a dedicated wire to each said tips, because there is not enough room in the body of the supporting structure for many wires. We propose the use of digital addressing the tips, so a smaller number of wires (say n wires) can select a larger number of electrode tips (2 power n electrodes). Using serial addressing the number of wires can be further decreased to a minimum of 2 wires, or 4 wires if using USB standards, or some similar small number, depending on the standard selected.

SUMMARY

We disclose a method and a means to fine adjust the position of electrical stimulating electrodes with respect to neurons, as in brain or spinal cord, or with respect to muscle, as in heart, with the objective to originating the electrical stimulation at a more precise location with view of improving its effect and of eliminating possible side, unwanted effects. In Brain, spinal cord and the like, our invention is capable of better selecting the neurons that are stimulated, in heart out invention is better able to produce a better heart squeezing sequence, thereby producing a more efficient heart pumping, when compared with prior art. Changing the electrode used for stimulation the position of the electrical stimulation with fixed electrodes may also be changed in a random way, also randomized time of stimulation, to prevent that a repetitive electrical stimulation cause the formation of networks and/or loops, which could become themselves sources of non-intended consequences, including involuntary motion but also including emotions and the like.

DRAWINGS

FIG. 1 shows a general view of the main embodiment of our invention using most of the current art features but with a translation feature capable of moving the picafina in and out of the brain. In this embodiment the motor can advance or retreat the picafina by approximately 140% of the distance that separates each stimulating ring-like pad at its distal extremity. The extra motion (40%) being to account for engineering safety, it being possible to have more or less safety margin without changing the substance of the invention. It is possible to advance or retreat by only 100% of the distance between electrodes, but in this case there would be no margin of error, usually not chosen by engineers. It is also possible to advance or retreat by less than 100%, but in this case not all points would be covered; it would be an improvement on the current art but not as complete an improvement as possible to make.

FIG. 2 shows a view of the proximal end of the picafina of our invention. In this particular case there are three holding screws but the same invention would work with more or with less holding screws, as it will be apparent to persons skilled in the art of mechanics.

FIG. 2a shows a top view of a skull with two burr holes for two implants, on the left and on the right brain, one of them showing the support device SUPP1, the other not showing SUPP1.

Figure 13:
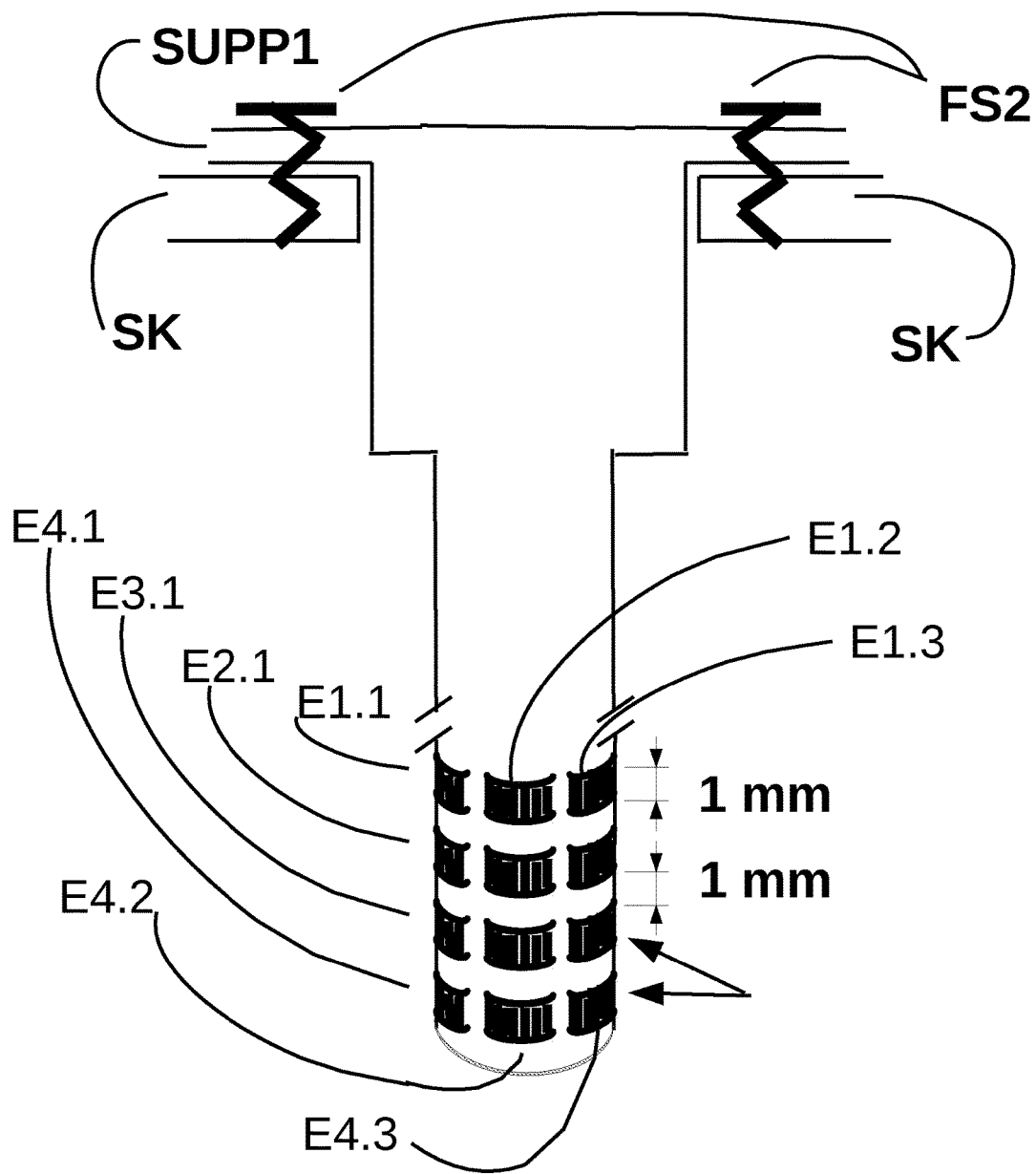

FIG. 3 shows a general view of the main embodiment which consists of an old art DBS lead, same dimensions as old art, 1 mm wide rings near the distal edge of the lead, separated by 1 mm distance. In this embodiment the screws are also 1 mm long (or 1.4 mm long with the 40% safety margin included), to permit that the metallic electrode rings travel over the 1 mm separating distance between each ring. With this dimensions, the lead covers a total of 5 mm possible positions to initiate the electrical pulses, some of these selecting one or another of the four rings, others by advancing/retreating the picafina device.

FIG. 4 shows a possible configuration of the picafina of our invention with the screw and tapped support and electrodes.

FIG. 5a and FIG. 5b show two possible relative positionings of the picafina with respect to the area of interest. In figure FIG. 5a the medical staff would turn on electrode number 4 only, to send electrical pulses towards the area of interest, while in figure FIG. 5b electrodes 3 and 4 would be energized, for the same reason. Note that FIG. 5 (a and b) display the relative position of the picafina of our invention with respect to tissues perpendicular to the main dimension (or theta-direction, angular displacement in normal cylindrical coordinates). FIG. 12 (a and b) display the relative position of the picafina of our invention with respect to tissues along the main dimension (or z-direction, displacement in normal cylindrical coordinates). The picafina of our invention allows for better adjustment of the stimulating point in both angular (theta) and axial (z) coordinates.

FIG. 6 displays an alternative embodiment of our invention in which there are two independent motors MOT1 and MOT2, each of which are capable of providing a rotational motion. Due to its particular mechanical connections, as common and known in the mechanical arts, MOT1 causes attachment SUPP1 to move axially, perpendicular to the skull, which then, through attachment ATT1 moves the second support SUPP2 up and down, together with SUPP1. ATT1 is capable of imparting translational motion to SUPP2 but not to rotate SUPP2. Rotational motion is independently imparted to the picafina of out invention by another motor MOT2, which turns the picafina supported by SUPP2. In this particular embodiment the electrical pads are shown as making an arc of 80 degrees each, with 10 degrees separation between each electrical pads, making a total of four pads around the circumference. The total number of pads in this embodiment is 16 (4 pads along each ring and 4 rings separated by 1 mm from each other). The number of electrical pads can be larger or smaller without changing the disclosure of the invention. For example, another embodiment could have 8 pads on each ring, each one encompassing an angle of 35 degrees, separated by 10 degrees, and more or less than four rings are possible without changing the principle of the disclosed invention.

FIG. 7. Distal extremity of the heart stimulator, or pacemaker device, here called cordum, with the multiple pads, or electrodes, which are the location from which the electrical pulse originate. The pads are selected with a digital or binary addressing system, as described in other patent application of some of the authors of this patent, which can be sent either in parallel or in serial form. The length indicated, h, shown as being between 1 mm and 10 mm, but these are just typical values, not intended as a limitation on the invention, as can be appreciated by the practitioners of the art, longer and shorter values are possible, depending on the particular situation, heart wall thickness, etc. The angle of the screw is also not a limiting parameter, the drawing simply indicating a possible embodiment out of a large number of other values, as it can be appreciated by the practitioners of the art.

FIG. 8, FIG. 8a, FIG. 8b display details of possible anchoring mechanisms for the motor and proximal extremity of the picafina of our invention. A connecting axle CON-AXLE with a hexagonal shape at the picafina, matches an hexagonal orifice at the distal extremity of the motor MOT1, similar to the standard hex screw drives and screws. Note that it is not necessary to have these parts with hexagonal shape, as a slot (similar to old screws and screw drives), or a cross (similar to Philips screws and screw drives), and star (similar to star screws and screw drives), etc. are equally acceptable, as it is appreciated by persons with knowledge in the art of mechanical connections.

FIG. 8c displays a longer CON-AXLE at the proximal extremity of the picafina of our invention, which can take the vertical motion in-and-out of the brain without decoupling from the motor. It is possible to use such a method which then keeps the motor MOT1 fixed, as opposed to figure FIG. 8, in which the motor MOT1 moves up and down along the slots SL1.

FIG. 9 displays a mechanism to allow for the insertion of the picafina at a position other than perpendicular to the skull. Often times the picafina is inserted at a small angle with respect to the perpendicular to the top of the skull (call this perpendicular "vertical"). A mechanism indicated allow such an adjustment to be made, as needed by the surgeon. Note the angle adjusting wedge ANG1.

FIG. 10 shows a blow-out of several of the parts shown in figure FIG. 9

FIG. 11 (a and b) show alternative possibilities for the cordum, used for heart pacemaking.

FIG. 12 (a and b) show the effect of the vertical (or z-direction, along the main dimension of the picafina) mispositioning of the picafina with respect to the region of interest, and the effect of our invention in correcting it. The reader is encouraged to refer also to figure FIG. 5a and FIG. 5b, which display the mis-positioning in the theta direction. Saying it in another way, FIG. 5 displays mis-positioning due to the picafina being on the side, or edge of the region of interest, while FIG. 12 displays mis-positioning due to the distal extremity of the picafina being beyond the region of interest. The former case (theta) requires that only part of a ring be selected, the latter case (z) requires that the ring in use be as close as possible to the center of the region of interest along the z-direction, or the long dimension of the picafina. Note too that for the z positioning, it is the best positioning that is sought, which is achieved with our invention disclosed here. Here we are using z and theta in the ordinary sense used by mathematicians to describe cylindrical coordinates.

FIG. 13. Second variation of the main embodiment.

DRAWINGS

LIST OF REFERENCE NUMERALS

EM1=electric motor which causes the translational motion of the picafina along its length FS2=Fixing screw, which fixes the supporting structure SUPP1 onto the skull.

Skull=self describing.

EM1=motor capable of moving the picafina.

EM2=motor capable of rotating the picafina of our invention.

MOT1=motor capable of moving the picafina.

MOT2=motor capable of rotating the picafina of our invention.

SUPP1=supporting structure, screwed onto the skull, which is fitted with a means to slide the picafina in and out of the supporting structure. In the main embodiment such a sliding motion is made by a screw.

SUPP2=supporting structure, attached to SUPP1, which serves as a support for a rotating device caused by MOT2

SR1=screw on the proximal end of the picafina of our invention.

TT1=tapped thread on SUPP1 inside which SR1 turns to move the picafina of our invention along its longitudinal dimension.

DETAILED DESCRIPTION

In the spirit of the USPTO requirement of making a complete description of the invention, we start with a definition of the crucial terms used in the description of the invention, so that the specification of our invention is best and clearly understood by any future user.

Artificial neural network. We will use the more specific term "artificial neural network" for the counterpart of the neural network implemented with solid state electronics and/or any of its equivalents. We will be using the commonly used words "neural network" on a more restrictive meaning than it is normally used of natural actual neural networks, that is, networks of neurons in a brain of some animal. cf. neural network.

Comprehensive random. Any of the variations of a true random sequence (q.v.) including true random (q.v.), quasi-random (q.v.), pseudorandom (q.v.), and "recurring random chopped sequences" (q.v.). In short, we are creating the term "comprehensive random", which is not defined in the mathematics literature, as any variation of a random sequence which meets the requirements of the clinical needs, that is, having enough changes in the sequence that the body cells have either none or at most too small probability of predicting the series, even if a computer with an ordinary skilled person would easily find the repetition pattern. When applied to a time sequence, comprehensive random acquires the normal meaning because the normal understanding of time is a number, while when applied to a change in electrodes. comprehensive random assumes that each electrode is assigned to a number, for example, a sequential number, which then is selected in a comprehensive random way.

Neural network. We will be using this words on a more restrictive meaning than it is normally used. We will use neural network to refer to natural actual neural networks, that is, networks of neurons in a brain of some animal, and will use the more specific term "artificial neural network" for the counterpart of the neural network implemented with solid state electronics and/or any of its equivalents. cf. artificial neural network Picafina. We create this term that is more or less similar to the currently used word "lead", which is dubious. Picafina is a particular electrode supporting structure, of the type used for DBS (Deep Brain Stimulation), but also used in a few other situations, which is generally elongated in shape, with a small diameter, adapted to be inserted into a brain or some other body structure or cavity, such that the stimulation locus is generally deep inside the body. We are generally interested in the proximal and distal extremity of the picafina, its inner body and the surface that encloses the inner body, on which are the fixed electrodes.

Pseudorandom. We use this term in the same way as it is defined in mathematics: a pseudorandom sequence is a sequence that is random but that repeats itself when generated again.

Quasi-random. We use this term in the same way as it is defined in mathematics, which approximately corresponds to the layman understanding of it being very difficult to predict the next number in the sequence but not impossible.

Random. We use this term in the same way as it is defined in mathematics, which approximately corresponds to the layman understanding of impossibility of predicting the next number in the sequence.

Recurring random chopped sequences. A sequence of numbers which is composed of a finite random (q.v.) or a quasi-random (q.v.) sequence that repeats at the end of the finite sequence. It is approximately what is known in mathematics as a pseudorandom sequence (q.v.). Such a sequence is very easy to predict, because it repeats the numbers, but would still suffice for a clinical application, because the cells would not be able to predict the sequence, and therefore such a recurring random chopped sequence would still work as a true random sequence for most clinical applications. The inventors believe that a sequence of as little as 20 to 100 random numbers that repeats over and over would do the trick for a biological application, which is an easy task to program.

Preferred Embodiment—FIG. 13

We will describe a main embodiment of our invention for use in DBS (Deep Brain Stimulation). Variations for use in more superficial areas of the brain, or for use in spinal cord, or for use as TENS devices (Transcutaneous Electrical Nerve Stimulation, pain control), or for use as heart pacemakers, etc. will be apparent to the ones skilled in the relevant arts.

We firstly make a shorter description intended for engineers and technicians, then a longer description for the layperson, or a person who is familiar with some of the aspects of the invention but not familiar with all of its aspects. Note that the invention involves more than one field of expertise, so the number of people familiar with all its aspects is small, which decreases the possible pool for the famous person "skilled in the art" well known to the patent offices worldwide. To compensate for this shrunk "skilled" pool we try to describe our invention with more details and from several points-of-view.

Explanation for Engineers and Technicians.

The theory discussed here is believed to be true, but the invention is not dependent on its truth, but only on the effects, which are amply verified by practice. The theory is discussed only to cause the reader to better understand the subject matter and the working of our invention. Deep Brain Stimulation is the name given to the insertion of carefully controlled electrical pulses in a precise position in the lower, or deeper part of the brain. The location is not an arbitrary choice, but it is rather the location that controls, or at least is involved in some way, with the particular characteristic that the neurologist want to modify. Given a characteristic to be changed, the position (or positions) in the brain which should receive electrical stimulation is fixed. This is because each thing originates in a particular place in the brain, whether it be mechanical, like the motion of an arm of the jaw, or emotional, as a feeling of love or fear, each one originates in one of several defined and known parts in the brain. Parkinson's disease depends on neural firings in a few positions deep inside, at the base of the brain, from where the name of the surgery originates. It turns out that it is difficult for the neurosurgeon to position the electrode at the exact target position, both because the desired place is very small, only a few mm along any direction, and also because the relative position of it, with respect to a fiduciary, fixed position on the skull, is variable from person to person, no different than the position of the tip of the nose being different, with respect to each ear lobe, from person to person. Ultimately the neurosurgeon knows that the placement of the picafina is only approximate. Old art solved this problem offering a choice of 4 rings (or some similar arrangement) to chose after the surgery finishes, each ring offering a different location for the electrical stimulation. Some of the improvement of our invention over prior art is partly the ability to move the picafina in-and-out, along its length and at controlled speeds, in order to produce the desired stimulation at the perfect position (figure FIG. 1). Another improvement of our invention over prior art is the possibility of producing the stimulation not along all directions (360 degrees around the picafina distal end), as most of prior art devices do, but along selected directions (see figure FIG. 4), as needed and discovered by experience, each patient requiring a particular stimulation. Our device offers the possibility of rotating the picafina along its main dimension to position the stimulating pads towards the optimal directions, as discovered by experience with each patient. The most simple embodiment of our invention uses one motion device only, while a more sophisticated version uses a minimum of two motion devices, one to move the picafina in-and-out of the brain, the other to rotate the picafina, in order to cause the stimulation along the most desired direction (see figure FIG. 6). The combination causes the stimulation to be delivered at any desired depth and along any desired direction, as needed for any particular patient making use of the device.

We will now describe two variations of a main embodiment of our invention for laypersons, also for use in DBS (Deep Brain Stimulation). These two variations both involve moving the position from which the electrical stimulation is injected in the body: the first variation involves physically moving the picafina to a new position on the patient, while the second variation involves keeping the picafina in a fixed position while selecting different stimulating electrodes (also known as pads), from which to inject the electrical stimulation. Though these two variations of the main embodiment are similar in that both involve changing the stimulation location, the objectives are different: the first variation is an adjustment to a generally fixed and repetitive stimulation point, while the second variation is a forever changing of the stimulation position, both in space and in time. While the objective of the first variation of the main embodiment is to best adjust the position of the stimulation point within the body of the patient, the objective of the second variation of the main embodiment is to forestall the possible creation of newly created self-sustaining neural networks (and/or loops) in the sense of Hebb (Robert Miller 1991). Variations for use in more superficial areas of the brain, or for use in spinal cord, or for use as TENS devices, or for use as heart pacemakers, etc. will be apparent to the ones skilled in the relevant arts.

For the first variation of the main embodiment the reader is referred to Figures FIG. 1, FIG. 2 FIG. 2a, FIG. 3, FIG. 4, FIG. 6, FIG. 8, 8a, 8b, 8c, FIG. 9, FIG. 10 and FIG. 12a,b, which display simplified views of the main embodiment of our invention for DBS. In figure FIG. 1 one can see a supporting structure SUPP1, which is fastened onto the skull by fixing screws FS1 (there are three screws in this particular main embodiment, but the equivalent results can be achieved with more or less fastening screws, as known by the people familiar with the art). On supporting structure SUPP1 there exists a tapped screw, or auger, which is part of the means to move a picafina-like device along its long dimension, in and out of the patient brain. This particular method is shown as an exemplary implementation only, as there are many methods which can achieve the same result of moving a piece axially, as known to the people familiar with the art of mechanical motion, as machinists with experience in lathes and milling machines, automobile repairmen, mechanical engineers, "handymen", or even to lay persons. One of the improvements of our invention over prior art is the capability of moving the picafina used in DBS into and out of the brain, as well as turning it around once inserted, to change the position and the direction of its electrodes or pads, from where the stimulating pulse originates. This particular implementation of a translating device using electric motor EM1 and EM2 is not the only possibility for our invention, which is not the invention of an electric motor, not the invention of a translation device, nor the use of a rotation device, but rather the use of a rotation device and of a translation device to achieve the goal of moving a picafina-like device to adjust the precise position of the delivery of the DBS pulse to the desired brain location. This adjustment is required by two factors. First the neurosurgeon cannot insert the picafina into the optimal position, which results that adjustments have to be made post-surgery to the stimulation site, and second because the picafina may move with respect to the brain, or vice-versa, needing later adjustment to correct for this. In one possible main embodiment there exists on the proximal end of the picafina a thread matching the female thread on supporting structure SUPP1 and an electrical motor to turn this thread. In other words, this means to move the picafina along its long dimension is an auger with female part on SUPP1 and male part on the picafina itself, with an electric motor on the picafina which is capable of turning the male part of the auger (the part connected to the picafina), which then moves the picafina along its long dimension. In a second possible main embodiment, shown in figure FIG. 6, there are two electrical motors, EM1 and EM2, where EM1 causes, due to the coupling, a translation only motion on the picafina, in-and-out of the patient's brain, while EM2 causes a rotation only motion of the picafina, rotating it around its main, long dimension.

In the main embodiment said means to move said picafina-like device is capable to move the picafina-like device over a 1.4 mm range, 1 mm being the separation between the electrode rings, 0.4 mm for engineering safety. This range corresponds to the space separating each of the rings that originate the stimulation electrical current in existing Medtronic electrodes (see figure FIG. 3) with an added arbitrary engineering safety margin of 40%. The reader will notice that if the screw can longitudinally displace the picafina by the same distance as the ring separation, all the dead space between two rings become reachable by the adjoining rings. Within the confines of the main embodiment, as described, with 1 mm wide rings, spaced by also 1 mm, at the distal end of the picafina (see figure FIG. 3) a 1 mm range of motion causes a total reach of 5 mm (discounting the added 0.4 mm safety margin) with the resolution (minimum longitudinal dislocation) of a few micrometers, equivalent of the advance corresponding to the minimum angular turn of the supporting structure and the screw pitch, which is not specified in this description but can easily cause a minimum longitudinal motion of 50 micrometers, roughly equivalent to a hair width. The invention preferred embodiment would provide a motion of 1.4 mm, corresponding to a 40% engineering safety margin, though this safety margin should not be considered a limitation of our invention, which works without it. In fact, the invention even offers some improvement over current art even if the motion is not enough to cover the full separation between two of the rings, such a case being also covered by our invention.

FIG. 2 displays a view from the top of the skull, where one can see the burr hole to access the brain and the circular flap SUPP1 which is screwed onto the skull by a plurality of screws. In the main embodiment there are three screws attaching the support SUPP1 onto the skull but persons skilled in the art understand that it is not necessary to use exactly three screws, it being possible to achieve the same result with less and with more screws, three screws being used as an exemplary concrete case which is not intended to restrict our invention.

Finally, figure FIG. 3 shows the simpler form of the improved picafina of our invention alone, independent of its attaching and moving mechanism. The simpler form is only capable of an in-and-out motion, with an associated rotation as the picafina moves in-and-out. A proximal end with screws used to turn and move it forward and backward, depending on the direction of turn by motor EM1, its elongated body and the four ring-like electrodes at its distal end, from where electricity can be injected in the brain to achieve the desired result.

Moving now to the second variation of the main embodiment, a possible hardware to implement the second variation of the main embodiment is shown at FIG. 13. FIG. 13 shows a picafina penetrating support device with a multiplicity of electrodes at its distal or stimulating extremity. Though the second variation may work with the old-fashioned ring-like electrodes shown in FIGS. 1, 3, 8, etc., these dinosaur-type electrodes would not be able to implement the objectives of the second variation to its fullest, because the dinosaur-type electrodes currently in use are so small in numbers that too few different sequences of stimulation sites are possible. Therefore the inventor recommends that the second variation be preferentially implemented with small electrodes as shown in FIG. 13. It is not necessary that the electrodes, or pads, for use on this second variation of the main embodiment are "rectangularly" shaped, as in FIG. 13, but only that they are "small", in this case encompassing an angular wedge such that there are at least a few of them at each z-coordinate (using standard cylindrical coordinates), and also on a small length along the picafina axis (z-coordinate). The "small" here is a relative, subjective measure. The second variation of the main embodiment of the invention is to cause an electrical stimulation that varies the stimulation locus in a random way, or, at least, following a sequence of stimulation sites that only repeats after a relatively large number of stimulation sites are visited. Anticipating what will be explaining in the sequel, this type of variation of the stimulation site is to prevent self-sustaining closed neural network loops, because the inventor has good reason the believe that the Parkinson's tremor is caused by one or a combination of several self-sustaining neural loops which are capable of generating efferent signals to the hands and other parts of the patient, this being the reason why "small-frequencies" (1 to 50 Hz) are not capable of blocking the tremor, while "high-frequencies) (>50 or 100 Hz, say, the typical 200 Hz) are capable of blocking the tremor.

Some examples of intended use.

One example of intended use of our invention is for the treatment of Parkinson's disease. For Parkinson's disease the electrical stimulation may occur on the Globus Pallidus internus (GPi) on the Subthalamic Nucleus (STN) or a few other sites at the base deep in the brain. For the similar problem known as essential tremor the usual target is the thalamus (T), but other sites are also targeted. In either case, the picafina is inserted in the brain until its distal extremity reaches the desired location (GPi, STN or T or other location determined by the neurosurgeon). Once the distal extremity of the picafina is at the desired depth, one or more than one ring is selected, by trial and error, to produce the stimulation, until the desired positive effects are observed. The first variation of our invention allows the extra possibility of selecting depths not covered by prior art devices, the depths that correspond to the dead spaces around the spacers between any two ring-like electrode in current art devices. as well as to produce the stimulation along some directions only, as shown in figure FIG. 5*a* and FIG. 5*b*.

Another example of intended use of our invention is the heart pacemaker. One of the possibilities to attach a pacemaker to the heart is to start from a generally neck located vein, from which a wire is inserted down onto the inner wall of the heart, and ultimately the tip of this wire is screwed into this inner heart wall. Prior art pacemakers use the tip of the device to start an electric pulse over a large surface area and symmetrically over the 360 degrees around it. Our invention as shown in figure FIG. 7, uses a plurality of pads (or electrodes) to initiate the pacemaking pulse. Choosing one or a group of electrodes (see figure FIG. 7) creates a pacemaking pulse at a precise depth on this anchored electrode, and towards any chosen direction, and along any arc angle desired, this being obtained with the appropriate selection of a subset of the electrodes on the cordum of our invention. It is well established in the art that the electrical pulse travels through the heart, usually from the sinus, at a particular speed and phase (that is, delay) along the heart muscle, causing it to contract in a particular sequence, which maximizes its pumping capability. For this pumping to be best replicated, the electrical pulse must be initiated in particular places and directions, which is not done in prior art. Our invention improves on this, allowing the initiation place of the stimulation pulse to be anywhere on the surface of the anchoring part of the pacemaker, at any depth and towards any desired direction. The selection of electrodes is made using a method disclosed in our inventions (INV1, INV2, INV3, INV4, INV5), which are part of this disclosure and are included here in their totality. Some of the pertinent parts of these inventions which are currently in the PPA and RPA stage are included at the end of this PPA for completeness but we request that their full text be considered as part of this disclosure.

For heart pacemaking the heart surgeon keeps inserting the electrode into the heart wall while observing the results of electrical pulses on an EKG (electro-cardiogram) machine, all the while looking for the best location. The first variation of our invention, which has isolated and relatively small electric pads to initiate the stimulating electrical pulses, offers the possibility, not offered in prior art devices, of stimulating the heart at a more defined location, which, in turn, causes a better contraction sequence of the heart.

Operation of Invention

First variation of the main embodiment of our invention.

The first variation of our invention operates adjusting the position of the implanted electrode both axially (in and out of the brain) and radially (rotation around its long dimension). A combination of these two motions adjust the position of the electrodes for optimal position of the electrical stimulation.

The first variation of the main embodiment of our invention operates moving axially the picafina of our invention, in and out of the brain, that is, along its major axis, by means of an electric motor EM1, which is located on the proximal end of the picafina, and rotating it around its major axis, by means of another independent motor EM2, to position the pads towards any desired direction. Motor EM1 is capable of turning the screw SC1 inside tapped thread TT1, causing the picafina to advance into or to recede from the brain, depending on the direction the screw is turned—advancing for a clockwise turn of the screw and receding for a counterclockwise turn of the screw (assuming a normal, right-hand screw as intended in the main embodiment, this being only an arbitrary choice, any type of screw being possible to use, including a left-hand screw). Motor EM2 is capable of rotating the distal extremity of the picafina as needed, rotation which is achieved with the turning of SC2 inside TT2, where TT2 is a tapped thread on support SUPP2. This motion of the picafina caused by the rotation of SC2 inside TT2 also causes an in-and-out motion, but the intended purpose in this case is to simply turn the picafina, so the thread may, for example, be fine, and in any case, once the motion is decoupled, MOT2 being responsible for the rotation part of the picafina adjustment, it needs to cause only 360 degrees rotation, or, adding an engineering safety margin of say, 40%, 504 degrees rotation. Persons familiar with the engineering art will immediately understand that a safety margin of 10%, or 25%, or any similar one are also in the scope of the invention, this suggested value of 40% safety margin being used only as an exemplary value not intended to limit our invention.

In the main embodiment motors EM1 and EM2 are located at the proximal end of the picafina, but this should not be taken as the only possibility, as it is readily appreciated by the practitioners of the mechanical arts, it being possible to have, for example, EM1 at the proximal end of the picafina, at the skull, and EM2 at the distal end, just before the electrodes, or any other combination.

Second variation of the main embodiment of our invention.

The second variation of the main embodiment of our invention operates modifying randomly the location of electrical stimulation (which electrode or pad is activated to inject electric current in the patient's body) while keeping the supporting structure (the picafina) in place, and/or also varying randomly the delay between the activation of one electrode and the next (the equivalent to a random frequency, which is an oxymoron, or no frequency if you want to think of frequency), and/or also varying the time width of the stimulating pulse. One alone, two or all the three are possible as second variations of the main embodiment. The reader is reminded of the basic difference between the first and second variation of the main embodiment: while the first variation moves the physical supporting piece (the picafina supporting structure), the second variation keeps the picafina stationary but changes which of the electrodes are energized, in effect changing the stimulation location without moving the picafina. This variation of modifying the stimulation location, that is, keeping the picafina supporting structure stationary while starting the electrical stimulation from electrodes located at several locations on the picafina's surface is necessary because the second variation requires a location change of the order of millisecond, which is not achievable with moving the whole picafina supporting structure.

From now on we will be using the word "comprehensive random" with the inclusive meaning of "random", "quasi-random" and "recurring random chopped sequences" and other similar variations. When varying randomly the delay between the activation of one electrode to the next, it may be better, from the clinical point of view, to vary randomly but within a minimum and a maximum values that is decided depending on the application and on the patient, or even the current state of the patient, which can vary over the years. Also, the time width of the pulse (that is, the time the activation electrical current is on) for the second variation may or may not be randomly changed, and also, if it is randomly varied, the selected values may better be kept within a certain range, between a minimum and a maximum values.

Repeating, the second variation causes from one to three changes on the electrical stimulation: firstly it implements a change of the location where the electrical stimulation occurs, with a change of the electrode that is activated, as time goes on, and secondly it implements a change of the times associated with the stimulation, this including both (1) a random initiation time with respect to any arbitrary time origin and also (2) a random time width of the pulse, that is, a random time when the pulse is on the "on" state. For example: E1.2, E3.1, E4.4, E2.1, etc (see FIG. 13 for the location of Ei,j, where i,j=1, 2, 3, 4 in FIG. 13, but a real picafina may easily have more then four electrodes around the axis and more than four electrodes along the axis), and a time delay between the electrical stimulation originating at E1.2 and E3.1, then a different time delay between the electrical stimulation originating at E3.1 and E4.4. then a different time delay between the electrical stimulation originating at E4.4 and E2.1, etc. Besides, the length of time each of these stimulation pulses is on may be different from each other and the value is randomly chosen.

The time delay between each stimulation event is fixed in current art, typically at a frequency f=200 Hz, that is, a period T=5 ms (period means the time for a full cycle, or the length of a wave). There are some more modern and advanced systems, following a varying but recurrent pattern as described by Prof. Peter Tass and collaborators. We think that the variation introduced by Tass is a very good improvement over the current stimulation method. In contradistinction to this, our invention discloses one or more of the following being modified in a random way for the clinical process, preferably all of them: (1) the stimulating electrode sequence, (2) the time delay between any two stimulation events and (3) the "on" time of a particular stimulation event. There exists a deceptively similarity between the first and second variation of the main embodiment, because they both use the same general feature of moving the stimulation point in the body, but the second variation causes a change of position of the stimulation source point that has deeper consequences than the first variation. The reason for this deeper consequences are explained in the theory section below, being related to the loops that the inventor believes to be at the root of all our mental processes, including the generation of the motor sequences at the brain—or at the peripheral nervous system, as at the spine.

Operation of Invention—Theoretical Section

In this section we present some theoretical proposals in support of the advantage of our invention over prior art. Part of the following theoretical evidence is linked to known experimental results, part is accepted in varying degrees by the neuro community, and finally, part of what follows is possible neurological mechanisms that are proposed by the inventor. The invention is not bound to any part of the theoretical support, but only on its effects on the subjects receiving the electrical stimulation, and if the theory, in part or totally, happens to be proven wrong but the results correct for another reason, then the invention still stands.

In what follows we will often make analogies with linguistics, that is, with the theory of language, and in particular with the work of Ferdinand de Saussure. Such analogy will be made for two reasons. Firstly, because it is a theory of thought, and therefore it is expected that it ought to have connections to the neural activity that supports it. Moreover, because it is expectable that the neural process that supports language ought to use similar mechanisms as the language itself created by the brain. Secondly, because for historical reasons linguistics has developed more than modern-type neurology and brain, and have therefore many more ideas and proposals to dig out from, polish and reuse in our field here of Parkinson's tremor. The reader is warned, though, that our analogies with linguistics, and particularly using the work of Ferdinand de Saussure, though it is accepted by a very large number of workers in the field of linguistics, it is denied by a strong American current, led by Noam Chomsky, who proposes that the *Homo sapiens* brain has a special hardware used for grammar, which is inexistent in any other animal, this being, according to Chomsky, why *H. sapiens*, and *H. sapiens* alone, is capable of speech. In other words, Chomsky and his followers believe that *H. sapiens* have two brains: the normal brain and a grammar brain. We reject this hypothesis, adopting instead the hypothesis that *H. sapiens* and all other animals have one single brain structure that adapted itself by Darwinian-style biological evolution along the time, and through Darwinian evolution to different tasks, including among these motor tasks and all other intellectual tasks, there including language (and grammar), visual processing, auditory processing and other alternative languages as well, as algebra, group theory and differential equations. We reject Chomsky approach to and model of language because of its smaller compatibility with Darwionian evolution (in any of its variations) and because it is a reductionist approach, while Saussure model is a systems approach.

We next bring to the attention of the reader two examples that give support to our theory of the brain in general, of the brain mechanism to produce motor, and Parkinson's disease mechanism. Our theory is, as it will be described in the sequel, based on neural networks in the shape of closed loops. We start now discussing prior work introducing neural network by the noted Spaniard Santiago Ramón y Cajal, then the work on loops by May-Britt Moser and_Edvard Moser (Norwegian University of Science and Technology) that brought them the 2014 Nobel Prize of Medicine. So, we start with a history and examples of the concept of neural network and neural loop assemblies in the brain.

There exists good evidence to support that the neural networks are the elements of both memory formation and of thoughts in general. The earliest proposal for this to be so that came to the attention of the inventor, is by Santiago Ramón y Cajal (RamonYCajal_1894), who, in his 1894 Croonian lecture at London, indicated that memories might be stored across synapses. Santiago Ramón y Cajal's proposal was later taken by Donald Hebb, who proposed the same thing in 1949. In his well-known book "Organization of Behavior" published in 1949, there is one single mention to Ramón y Cajal at page 230, but the inventor sees more of Ramón y Cajal in Hebb's book than the little short mention at page 230. Hebb became a very famous neurologist but the inventor never found any writing by Hebb giving sufficient credit to Ramón y Cajal for the initial theoretical proposal of networks for memory formation and to the work that brought fame to Hebb. Hebb's work eventually became, in many slightly different incarnations, the backbone of a good deal of the current work in natural and artificial neural networks, including some of the work on the current art computing known as "deep thinking". For some reason that escapes the inventor, the work by Santiago Ramón y Cajal has been forgotten, and the work by Donald Hebb is generally taken as the starting point for the current flood of work on neural network. This may have occurred because Hebb's book ("Organization of Behavior") is very well written, bringing together several works from different neurologists before him. The inventor considers Hebb book a good, well written synthesis, but relating to neural networks it is not a true original work.

More recently, May-Britt Moser and_Edvard Moser (Norwegian University of Science and Technology) have detected hexagonal planar loops that they showed to be associated with spatial memory and location mechanisms. We have read explicit mention to planar loops in several of the Moser's works and no mention to non-planar loops. We posit non-planar loops, though, and we cannot understand why the Moses propose planar loops, because planar loops are limited by topology to a restricted configuration and worse, loops sprouting from a particular point may be not closeable if it is confined to a plane due to existing loops, or may be only closeable via narrow corridors that would make them unlikely to close. For this mathematical reason we are absolutely convinced that the loops ought to be non-planar. The Moses got the 2014 Nobel prize for their work with loops and memory.

After this mention to prior work on neural networks and loops we want to bring up a second concept that is crucial to our model, which is the electrical resistance to the electrical current flow through the neural network. So, this is another line of thought, independent of the loops, and a second leg on which our model stands. It stands to reason that when the neuro people mention strengthening of the synapses they are introducing a biological term for what is known in physics and engineering as a resistance change—a decrease in resistance if the synapse is strengthened, so the two concepts move numerically in opposite directions, the synapse strengthening being equivalent to the electrical conductivity. The decrease in electrical resistance across the synapses is the most fundamental mechanism of memory formation both according to the much earlier work of Ramón y Cajal, that proposed a strengthening of the connections between the neurons, by the work of Donald Hebb and many others recently, by much of the current neuro work and by the theory being proposed by the inventor. Besides the change in perspective, from synapse strengthening to resistance, we are also introducing another element in the mechanism thought process and memory formation, and for the mechanism of neural motor control, which is the capacity of the neurons to generate energy to keep the neural network running, a point that has been forgotten by the neuro guys of today.

The method proposed by the inventor for all mental processes includes (1) the loops, and (2) the existence of a minimum of electrical resistance along a given path that forms a loop, and (3) an energy source for the loop continuation. Let us focus our attention now to a particular path of low electrical resistance, call it loop1, as compared with any other resistance along any and all other possible paths, loops or open paths, that uses any given node of loop1. If this occurs for a particular loop, say loop1, it follows that once a current starts on any node of loop1 it necessarily circulates around loop1, since to go outside it would be a path of larger resistance branch, back to its initial neuron, then around the same loop again and again.

We propose a correspondence of each idea with a loop, in the sense that to each idea there corresponds one or several loop(s). In other words, using Saussure's concepts, the loops are the signifiants for each of the possible ideas, or the signifié.

The loops become then the physical support of the ideas. The reader will notice that the possibility of electrical currents leaks to the outside of the loop is the mechanism of idea associations (that is, loop path interconnections within the loop representation space). Of course that this can only happen if the loop is either resistanceless (as in a superconductor, which is precluded to be the case), or if there exists a mechanism for energy generation inside the loop. Now, such an energy generating mechanism does exist and is well known: ADP, glucose, etc., the details of which are well known by the bio community. Therefore, acting together with the natural energy input in the loop system (the neural network) the electrical pulse propagates from one neuron to the next, causes a self-sustaining closed loop, which continues forever or until something stops the current from circulating inside the loop. The combination of a plurality of loops, in turn, is what determines the memory in the sense that the loop that starts with the sight of a dog, with the loop that brings back the knowledge that it is an animal that often dislikes cats, with a loop of a remembrance of being bitten by a dog in childhood, plus etc. determines the idea of a dog for one particular person, while another person may have loops that start with the sight of a dog, loops that brings back the knowledge that it is an animal that often dislikes cats but with a loop of a remembrance of a sweet dog that were best friends of this other person in childhood, which determines the idea of a dog for the second person. These two hypothetical individuals have different views of a dog, yet they both know that the feared animal for one is the same as the lovingly animal for the other, the difference being prior experiences stored in loops that are associated with fear in one person and with love in the other person—but they both are dogs.

Keeping in mind that the difference between a chiwawa and a cat is much less than the difference between a chiwawa and a doberman (the chiwawa is closer in appearance to a cat than he is to a doberman), while all humans would call both the chiwawa and the doberman a dog, and that the difference between a German shepherd and a wolf or between an Alaskan husky and a wolf is very small, but humans still call the former dogs and the latter wolfs, it becomes necessary to accept that what characterize any animal as belonging to a group is a large number of characteristics, more than just the physical appearance. This larger number of characteristics, each one being a loop(s) of its own, is what determines a dog to be a dog. We want to keep in the mind of the reader that these linguistics observations are a preparation for our model of motor control in general and Parkinson's disease in particular, which, as said above, ought to follow the same mechanisms as language does if one assumes that biological evolution evolved one brain that is used for language and motor activities, as opposed to two brains, as proposed by Noan Chomsky (a separate brain for grammar that only *H. sapiens* supposedly would have).

Let us assume that the inventor is correct in the mechanism that both memories and all thoughts are stored in loops and let us analyze these loops. We highlight here that these considerations do have consequences for the treatment of Parkinson's disease if we are to assume that we have one brain, instead of one brain for thinking and one different brain for motor activities, which is our working assumption, as is discussed in several parts of this text. It is here worth to specify that when we state that we believe that we have one brain we mean that we have one type of brain which evolved, while we are aware that different activities, for motor activities and information processing occur at different parts of the same brain which have the same general structure and organization. Any loop is a closed set of interconnected neurons such that one of them eventually bites its tail back: N1 (neuron N1) connected (among others) to N2 (neuron N2), N2 connected (among others) to N3, N4, N5 . . . -Nj-1, Nj, Nj+1, . . . Nk, Nk connected (among others) to N1, where Nk is connected back to N1 while, of course, possibly also connected to many other neurons branching out of the loop, but yet forming a closed loop, as a ring. The actual physical shape of the loop is immaterial for the mechanism: a circular loop, a hexagonal loop, an octagonal loop, etc. The number of elements part of the loop is immaterial as well. Also, loops are most likely not contained in a plane, so it is not really any of the named planar figures of geometry. This point that the loops ought to form non-planar structures is important for the mechanism because the non-planar loops can be arranged in a much larger number of combinations (that is, more available memory loops), because if the loops are non-planar it is possible to avoid crossing loops to be interfering with each other. The non-planar loop mechanism proposed by the inventor is akin to a printed circuit with more than one layer and with "vias", which are routes that link one layer to another layer while preventing the elements of the loops to touch each other. So, we do not expect the loops to be necessarily contained in any plane. The inventor is also aware that some non-planar loops are not topologically equivalent to any planar loops, as, for example, two rings that pass through each other inner part, or a ring with keys in it, neither of which can be continuously deformed into a planar configuration. Once the sum of the resistances between the synapses from N1 to N2 to N3 to . . . to Nk to N1 are such that the electrical current that is started anywhere in the loop stays in the loop to its starting point, from where it recirculates the loop, then it follows that the loop is a self-sustaining element—as long as the neurons and associated supporting cells are capable of generating enough energy to replenish the energy loss due to the equivalent of Joule heating, which, in this case would be electric current (ions) that are captured by the cells and get lost from the electrical current system. This self-sustaining characteristic is crucial if the loops are capable of storing memory of events and also for the loops to guide persistent pattern of thoughts as well. Then, by extension, the loops that can keep currents within it for long times may also be responsible for the motor activities of all animals, including humans, and including involuntary motions and even motions against the will of the animal or the person, as the Parkinson's tremor is. Another characteristic of the loops that is worth to bring up here is that each motion is caused by the combined efferent neural current to the appropriate muscles necessary to cause the particular motion, but because each motion may have subtle muscular variants that cause the same overall result, each person develop a particular loop sequence that causes a desired motion (say walking) using a particular subtle combination of muscles out of the myriad of possible combinations that achieve the same result, but once the brain learns one way then it becomes fixed so a particular person always use a particular combination of muscles to cause a certain general motion. This is the reason for the gait, the particular way of walking, or moving the hands adopted by each person and by each animal too.

The self-sustaining capability is a crucial characteristic of the loops, and one that has not been described before (but the inventor is just a physicist and so, a newbie in neuro things). This state of affairs occurs whenever the resistance to the next element of loop (of the ring) is sufficiently small that the neurotransmitters shot to the next element in the loop are enough to fire this next element to activation, and that this is so for all elements of the loop. It is here important to clarify that this does not mean that the firing is limited to the loop, not at all, not by any means. In fact, the theory of the mind proposed by the inventor requires that at some elements within the loop, and most likely at many elements within the loop, extra synapses also shoot out to other neurons outside the loop, some of which, in turn, may be part of other loops that will be activated together with the initial loop above (N1, N2, N3, . . . Nk, N1). So, in the example above, there would exist loops that detonate with the sight of a dog, which may cause the initiation of loops that detonate the idea of it being an animal that dislikes cats, etc., as many other loops as there are dog characteristics for the person in question. Also, the loop related to dog that stores the information that it is an animal that dislikes cats is also connected to a large number of loops all associated with cats, and so on ad infinitum.

*Homo sapiens* have also, and in this more or less alone among other animals, the capacity to create loops for words (dog, or chien, or cane, or Hund, etc., depending on the language the person happens to speak being English, or French, or Italian, or German, etc.), and these words-type loops are important for humans. This is important enough to repeat it: besides the loop that is the signifié of dog there are one or more loops that are signifiants for the same dog, one for the loop associated with the sound "do-g", if the individual happens to speak English, perhaps the same or another loop for the sound "ch-i-an" if the individual happens to speak French, etc. These word-type loops are capable of connecting to other loops for other words, in such a way that verbal logical statements about dogs can be generated. The inventor believes that it is the connection of all these concepts, signifiant using the concepts of Saussure (Saussure_CoursDeLinguistiqueGenerale) that creates the meaning of language. The language is a structural system. Again these comments are pertinent to the patent, because they are the equivalent and the guide signs for the motor mechanism, including the Parkinson's tremor. It is our contention that in fact these loops are the hardware counterparts of the signifié of Saussure, and that they join together to make meaning of things in the same way as described by Saussure. In other words, these signifiants have their physical counterparts in the loops described above— so, to each and all of the available signifiés, there exists one loop or a set of loops which are one of the representations of the particular concept or idea, that is, of the particular signifié. Of course that these loops may be interconnected— as all ideas are. This last point is important to establish the viability of the mechanism because it stands to reason that the mechanism proposed by the inventor automatically creates the interconnection of all ideas and concepts. The intersection of the loops, in turn, mirrors the intersection of words in common language, so the loops are, according to the our theory, the physical basis of language and of all other mental process, including the mechanical ones as the desired moving of the fingers to type this text, and the undesired shaking of the full hand of a patient suffering from Parkinson's disease. These latter loops are our concern here, because they may explain the mechanism that underlies the invention and also suggest mechanisms to block the Parkinson's disease shaking. As the intelligent reader knows, it is foolish to look for a solution to something without a describing theory of it.

Our theory also postulate that these word-loops cannot be manipulated by animals other than *H. sapiens* because to manipulate the loop it is necessary to actively connect it to associated loops, as connecting the loop(s) used for dog somewhere in our heads to the loop(s) used for cat, and also, above all, to actively make use of them. By actively making use of the loops we mean to use them to cause a sound (speech) that in turn causes a feedback that confirms that the loop that caused the sound was indeed used correctly, or the equivalent method of sign-languaging the loop, or any of its equivalents.

Making the connection to our Parkinson's tremor problem, this is the mental-logical-grammar equivalent of a child learning to walk. Children just try until they discover by trial-and-error how to move the leg (that is, to walk), the neural counterpart of what is the firing of this or that neural loop until the walk happens. *H. sapiens*, and *H. sapiens* only have a mechanism to try the words using his large and wide capacity of making different sounds. The counter-examples of Washoe and friends described by Roger Fouts (Roger Fouts "Next of Kin—What Chimpanzees Have Taught Me About Who We Are") and similar examples described by Jane Goodall and others, only add to our assertion, because these fall in the general area of deaf *H. sapiens*, as their chimpanzees and gorillas friends did learn sign language with a large vocabulary and became able to express feelings and emotions, to have empathy with the suffering of a human (Fouts), and even to lie, this latter two (to have empathy and to lie) observed by Fouts and reported in his book, articles and other publications. In the absence of the wide range of sounds that *H. sapiens* can make, and since dogs have no fingers to use sign language as our cousin apes do, it follows that dogs can learn the meaning of words (and everybody know that dogs do learn a large number of isolated words), but in the absence of actively using the words, dogs cannot construct grammatical sentences, and with them the ability of making logical analysis as a chimpanzee can, as shown by Roger Fouts and others. Lacking words, my dog Boomerang can have inner feelings, but he is not capable of logical analysis. He is also very intelligent, but intelligence alone, in the absence of active use of words, which alone would allow him to construct sentences and observe their consequences (as a child learning to talk does), is not enough to allow him to make a logical analysis. Boomerang is such a beautiful and sweet dog, he can make no logical analysis because he lacks the means to try words in an active way, but also without words he has no malice, he cannot lie as Washoe die lie to Roger Fouts, this being why dogs are worldwide considered to be the only true friends of men and women.

We want here to highlight that as Saussure implied, there is no logical analysis without words. It is false to believe that we first make a logical analysis then after we speak the logical analysis just made. Rather, both are born together. If the reader doubt this statement he/she needs to find an alternative way to make the logical analysis without the words used to express it. This observation is no different than the manipulation of the symbols to solve the pair of algebraic equations that represents algebraically the English word statement: the sum of the ages of a father and a son is 65 and the difference of their ages is 25; what are their ages? This is a trivial problem if written in the algebraic language, it is in fact such a straightforward problem that can be solved without thinking. Any language, of words or of mathematical symbols, allows for the manipulation of its symbols to arrive at conclusions.

The above observations have a place in the theory of animal motion, voluntary motion, as walking a dog, or involuntary motion, as heart beating or Parkinson's tremor, which is our intention here. Therefore, as much as the creation of language grows out of the intersection of the loops and their interconnection to other loops, the creation of body movements also grows out of the intersection of loops and their interconnection to other loops as well. One of the evidences that this ought to be so is that, in the absence of a separate soul that commands the body and mind, a soul that leaves the body at body death, it is inconceivable that there would be two different mechanisms (two brains so to say), one for mechanical motions another for verbal ability and sentence construction. Both language and movements are learned by trial and error, out of the intersection of a multiplicity of loops. In this context, the involuntary motions, as the ones that affect persons with Parkinson's disease, are a consequence of loops that become too strong to decay on their own, as happens on health persons that do not shake their hands. In a sense, the involuntary movements that affect people with Parkinson's disease are the motor equivalent of the fixed ideas that affect some people that keep washing their hands time after time, or having the feeling of being followed in the street in the absence of any evidence for it, or the belief that homeless persons are dangerous, this later being a widely held belief in US. All of these are garbage thoughts, as much as Parkinson's tremor is garbage motion. It is worth to remember here that most people are subject to involuntary movements, which are the gaits of each of us, and if the reader pays attention to it, he/she will recognize that we are capable of picking up and recognize the particular ways that our friends and acquaintances walk, their particular body waving, etc. I can state the truth of this because due to poor vision and other events that happened in my childhood, I have developed the habit of recognizing the gait of people to make up for the decreased ability to recognize their faces. Likewise we all are subject to fixed ideas to some extent. For example, most persons in the western world, living under capitalism, especially in the United States, have a fixation on increasing the number that is written by the bank on the box of their bank account, and they consistently act as if this were a worthwhile endeavor (to increase this number), in spite of the fact that there is plenty of evidence that such a belief is false, that there is scant gain to increase that particular number, and the little gain that there is, does not justify the effort and suffering caused to achieve it. The inventor wants to highlight here that far from being supererogatory, the comparison between ideas and motor activities is important for the establishment of the cause of Parkinson's disease, this being why we point out their similarity here. We remind the reader that to this day there is no theory that attempts to explain Parkinson's tremor, and that if our theory is correct then our theory will pave the way to find a cure for the tremor, because it will be a work towards a known objective: to disrupt the loops that cause Parkinson's tremor.

Memories, and also thoughts, all our thoughts and memories, and the thoughts and memories of Boomerang as well, are then, according to the inventor's theory, the particular set of linked loops that fire together. Note the point here: a thought/memory is not one loop alone, but the particular set of loops that are set alive due to some particular initial excitation. Such a system would, among other things, explain why my memory of 3.1415926535897932384626 etc. is partly similar to other pi memories of other people, yet still not the same memory as theirs, as most people remember a smaller amount of digits and a few have memorized even more digits. This would also explain why this number may be associated in English, and English only, to the desert known as pie, while not being associated with the same desert for Chinese and Russian speakers, the association being due to a language coincidence that occurs in English and English only. All these and any other conceivable association between the abstract number pi and its association in the brain of each individual determine what is pi for that particular individual. Likewise, a good number of people will agree that the concept of marijuana is different in the minds of an occasional user, particularly a person entering retirement age now, who went to college in the 60s-70s in US, and the mind of a much older person, perhaps in his/her 90s who never used it. The inventor believes that in all these cases, the number pi, the weed, and the Parkinson's hand tremor, it is the associations that give sense to the concepts and also to any particular motion of the hand and all its small variations, and that the associations are physically associated with interconnected loops in the sense described above. For the linguistic case this is only partly new observations, its roots being in Saussure's vision of linguistics, in particular between the connection and the interplay between the signifiant and the signifié, and for the motion case, in which our theory posits that a number of loops set in association is the cause of the tremor. The inventor believes that this is a new proposal for both the mechanism underlying Parkinson's disease and the individual gaits adopted by each person as well—and also for the mechanism underlying fixed ideas. In fact, the inventor believes that this also underlies his mental process that cause these words to be typed and the mental process of a *Drosophila melanogaster* that is fleeing an attack by a *Homo sapiens*.

Another leg on which the mechanism we are proposing is based is the energy—the source of energy for the continuation of the process. If we can give proof, or at least credible evidence for an energy source then our proposed mechanism gains credibility. This is then our next step.

Energy is required for a closed loop system to continue, because energy is spent for this proposed system to keep on going, as the current loops need some energy source to replace the natural energy losses due to the electrical resistance to the propagation of the currents, not only inside the neurons but the energy lost by ions being dragged outside and next to the neurons by the ionic current inside the neuron, and also at the synapses as well. It is here worth to point out that the concept of synapse strengthening that is advanced and defended by a large fraction of the neurologists, fails to acknowledge that there are resistance to the current flow at all points of the path, so our change of perspective from synapse strengthening to resistance is more than just a name, because the resistance includes other phenomena that are clearly in action: the energy losses due to collisions as the ions propagate inside the neurons and alongside them too. Indeed, as the ions propagate inside and outside the neurons, they suffer scattering and are therefore subjected to the same mechanism that causes the Joule heating of electrical networks. In this case, the necessary energy comes from the chemical energy available for the brain's workings, which ultimately is the energy stored in glucose, ATP, etc., in fact, the very energy that is measured by the fMRI (functional MRI), which measure the energy generation with labeled isotopes. Since fMRI is an accepted standard technique to measure brain activity, it follows that all the neuro community accepts already that there are mechanisms at place that occur at the site of brain activity—only that they do not know about the loops yet, hahah . . . . We propose that the glucose, ATP, etc. act as the repeater stations of the telegraph, or the telephone system, keeping a viable current in circulation in the loop in spite of the losses due to ion scattering and other similar events.

It is here worth to highlight that the proposed mechanism does not require any new development within the cellular system, as the known mechanisms already developed over the evolution of all life forms accounts for cellular energy generation for locomotion, for heart beating, etc. and that the proposed mechanism simply uses the existing structure already in place for other reasons. It is the same mechanism used for muscle contraction, the same mechanism in place that caused me to have sore legs for several days after I ran the 1984 New York City marathon, or that causes Boomerang to be limping today from sore legs due to him chasing too long a radio controlled electric car yesterday at Stoner Park. But we cannot have sore brains for thinking too much because there are no pain detectors in the brain, and few people think deep anyway!

Still on the energetic issue, it would be generally expected that more energy is spent to keep the initial loop running (N1, N2, N3, . . . Nk, N1) than the energy that leaks out of the loop, which is related to the accessory loops. For the case of thoughts and memory, this is necessary if the initial loop, that is, the initial motivation, is to be kept in mind, but this is not always the case, as we all know that our minds wonder out of the initial objective—a process that we can control if we have the necessary maturity to implement choices. For the case of motor control, on the other hand, the neural requirement is that the loop be temporary, because the motion is virtually always for a short time, so we expect that the loops associated with motion control to be short lived. Parkinson's tremor, on the other hand is not short lived, what lead us to postulate that it ought to be relatively easy for the motor loops to cross the barrier to become long lived, as the thought loops often are, what, in turn, explains the large incidence of Parkinson's disease. We expect that with age something happens that hinders the patient from controlling the motion, one of the few things associated with Parkinson's disease that is not explainable by our theory for the process but may be simply a decreased ability to produce dopamine. We do know that the decreased access to dopamine is one of the causes, though, but why this decrease happens we do not know.

As hinted above, an associated concept, valid for both thoughts and motor activities, is the electrical resistance. The electrical resistance ought to be smaller within the loop than that all the other possible pathways leaving the loop, with possible leaks, as long as the leak is smaller than the energy generated inside the loop by the creation of new currents minus the energy loss by the equivalent of Joule heating generated by the ions propagating through the loops. Indeed, unless the total electrical resistance of the loop, that is, the sum of all the resistances of all the neurons within the loop and the equivalent resistance at the synapses, is smaller that the electrical resistance of any other path that leaves the loop, the current loss to the outside the loop would be too large to maintain the loop in the stead state that our theory requires.

Repeating what was said above, it is important to remind the reader that energy has to be added into the loop for the loop to exist, and there are mechanisms for this, associated with the energy stored in the multitude of neurotransmitters, which is well known to the community of neuro guys. Indeed, there would be no closed loop if the electrical resistance for a current were not smaller as long as it propagates within the loop than the resistance that it would see if it were to leave the loop. The reader is here referred to the physics 101 problems involving Kirchhoff's circuit laws to solve for the unknowns in a network—they finally found an application, uff!

Memory, in turn, ordinary memory, as the reader memory of his/her birthdate, or the memory of this text in the mind of its readers (which hopefully will occur!) is stored as an association of such loops, and so is a particular sound sequence to be made to evoke a domestic animal that barks and wiggles the tail when happy, and the several different sound sequences to be made to evoke the same animal depending on the person being in UK (dog), France (chien), Italy (cane) or Germany (Hund)—which are different sound sequences. These different sounds can easily be linked by other synapses that make these four words memories interlinked, all the while they are associated with the same particular domestic animal. These different sounds, associated to the sound "dog" are associated to the sound "dog"/"chian"/"cane"/"Hund", sounds also depending on the person being in UK (cat), France (chat), Italy (gato) or Germany (Katz)—which are different sound sequences too. The inventor proposes that, as hinted by Saussure, it is the complete association of "dog" with "cat" and many other concepts that creates the concept (signifié) of "dog", and that this so to say software concept (from Saussure's linguistic mechanism), is associated with the hardware concept of the loops that we are proposing. We posit that the loops we are proposing are the physical equivalent of each of the isolated concepts that together create the linguistic world. The relationship of the first set of sounds (dog, etc.) acquires its meaning with their association of the second set of sounds (cat, etc.) and all other memories of dogs that is characteristic of each human, all different from one person to the other, which, in turn causes that the meaning of "dog" is different from person to person, though there exists a general meaning that is the same, which is shared by most persons. If our belief is correct that there cannot exist two different brains, one for thought/memory and other for motor activities, than these comparisons and analogies with linguistics, which is a field more advanced than the not yet existing science of motor mechanism, are illuminating and may indicate the correct mechanism that acts on the brain to orchestrate the motion of all animals, including the motion we are interested for this patent application, which is the undesired, uncontrollable tremor of Parkinson's disease.

Now back to our invention, the inventor also believes that the mechanism underlying Parkinson's disease, which is not known at present, is precisely these loops. The inventor is proposing that Parkinson's disease is the consequence of self-sustaining loops that are set in their course in the regions of the brain that are currently attacked by high frequency stimulation by DBS, and that all the mechanical function of the brain works in the same way: closed loops that are connected to the efferent neurons that cause the particular desired motion of the particular desired muscle (efferent neurons being the name used by the neuro guys to mean the neurons that conduct electrical pulses from the brain to the periphery, or to the muscles, etc.). Parkinson's disease then would be the final fixation of some loops that are near the particular neurons involved in the particular motion of the particular extremities (as the hand). If this were to be true, as the inventor believes to be the case, then the mechanism of Parkinson's disease would be the eventual development of one or more loops that are connected to the efferent neurons that cause the tremor—or that are indirectly connected to them. This would then explain the mechanism of DBS high-frequency electrical stimulation—which is unknown to this day: it would force a series of other neural paths that would (1) drain the force out of the loops that are causing the tremor and (2) superimpose more (electrical) spikes on these efferent neurons, which are of a high enough frequency as to make them ineffective for causing motor action (typically most known neural information is carried by low frequency spikes, the inventor knowing of no high frequency spikes associated with any neural carried information). In the past the neurosurgeons, surgeons that they are, trained to cut things out, simply cut out and gave to the cat pieces of the brain of the poor patient, until Benabid introduced the high frequency stimulation, high frequency here meaning f=~200 Hz.

Moving now to a recent improvement on the currently adopted fixed frequency DBS, Prof. Peter Tass and his associates in Juelich, Deutschland, recently proposed a complex stimulation sequence in several incarnations and modifications, generally called resynchronization therapy. The inventor much like the work of Peter Tass. It is the opinion of the inventor that resynchronization works better than standard old fixed frequency electrical stimulation because this latter, fixed frequency stimulation, may eventually foster the establishment of another new loops at many of the sub-harmonic frequencies, which is to start the Parkinson's symptoms all over again, while resynchronization, changing the pattern of stimulation, as it does, is less likely to generate new self sustaining loops. On the other hand, resynchronization still includes recurrent patterns of stimulation, in the form of one of the chosen frequencies or of their multiples and linear combination of them.

As a solution to these problems that are a direct consequence of the mechanism of Parkinson's disease proposed by the inventor, the inventor proposes that the best solution is to stimulate the brain instead with a random electrical stimulation pattern—random in both (1) electrode choice and (2) in the time of application of the stimulation pulse, and this latter in both the time interval between any two pulses and in the length of the pulse as well. The reason for random stimulation to be superior to both dinosaur old-style fixed frequency stimulation and to the much better Peter Tass resynchronization therapy, is that random stimulation starts no periodic cycles that may cause a self-perpetuating neural loop that may eventually continue on a self-maintaining loop, to cause impulses down the efferent neurons that will cause the tremors—or other undesirable results. It is here a good place to point out that luck is on the patient's side, in the sense that a true random stimulation is not necessary. If it were so, a complex software would have to be written, as true random numbers are difficult to generate. In this case of electrical stimulation for the suppression of neural loops, a pseudo-random number generator, for both stimulation location (which electrode becoming active as time passes) and timing (as the delay from each electrode activation to the next one), is all that is needed, because, unlike the lottery, which is watched by people trying to detect some cycle in the numbers with good computer time series analysis, hoping to guess the next winning number, the neurons have no particular interest in starting annoying loops, and so a pseudo-random number generator, which is easy to code, is all that is required. We are then defining the concept of comprehensive random sequence (see definition at the beginning of this specification) to cover many of the possible acceptable variation of a true random sequence that are acceptable for the clinical applications of the invention. Because of this, the random stimulation is easier to code than the resynchronization therapy proposed by Peter Tass—besides being better for not risking generating any further loops.

For reasons discussed elsewhere by Sergio Lara in "Considerações sobre o mecanismo de funcionamento do cérebro" to be submitted to the Anais da Academia Brasileira de Ciências, my dog Boomerang masters a too limited set of words which are insufficient to construct logical statements, and as a consequence of this incapacity of constructing logical statements with words (which are physically supported by neuro loops) Boomerang is capable of having fear of a person who once beat him, but is not capable of analyzing the fear with words and make a decision on whether the fear is still warranted in the current situation or not, because such an analysis can only be made with words connected in sentences to construct a logical analysis, as opposed to an inner feeling. This necessary connection between words and thoughts was clearly shown by Saussure in his "Cours de Linguistique Generale", and while it is widely accepted by a large number of persons that investigate languages it is far from being universally accepted, and it in fact generate more heat than an intellectual would like to see around what is a purely intellectual pursuit. Among others, it is vehemently denied by Noam Chomski.

Assuming that it is not credible that there are two brains, one old for motion, and another brain for speech and word manipulations, the inventor believes that the motor mechanisms ought to share the same mechanisms as the one used by the brain with the word manipulation, an assumption that is one of the guides we propose for attacking the tremor of Parkinson's disease. In other words, the inventor believes that actions happens according to the same mechanism of words and thoughts. This is true for voluntary motion of body parts, as the finger to type this sentence and the eyes motion to follow the result on the monitor in front, and for partially involuntary motions as the lung inhaling/exhaling, which can happens both involuntarily and voluntarily, and for totally involuntary motions, as the heart beating or the complex mechanism that determines the blood pressure. All these motions must be and are a consequence of neural loops, some that occur exclusively due to our volition (as the typing I am doing now), some that may occur with or without our volition (as the lung cycles), and others that occur without our volition (as the heart beating). These considerations may be considered trivial, and they indeed are trivial in isolation, but their extrapolation to Parkinson's disease are simple and have not been made yet. It is worth to point out that the extrapolation of these considerations to Parkinson's disease are not a trivial matter, because currently there exist no theory for the mechanism of Parkinson's disease, and a correct theory of Parkinson's disease would have an impact on the proper method to fix the tremor associated with it. In the case of Parkinson's disease, the inventor believes that the currently used fixed frequency electrical stimulation with DBS, with frequencies of the order or 200 Hz, causes spikes in the neural networks that are too high a frequency to excite hand tremors, so the undesirable low-frequency spikes that cause the tremors of Parkinson's become buried in the high frequency artificial spikes, causing that no tremor occurs, because the muscles cannot respond in the 5 milliseconds period of the 200 Hz artificial electrical stimulation. At the same time, though the 200 Hz artificial electrical stimulation is too high a frequency to directly cause neural spikes that detonate efferent neurons to cause the hand to shake, they still can, in time, cause the establishment of what we call "side loops", which are the loops at sub-harmonic frequencies that are set on by current that leak out of some prior existing 200 Hz loop created by the artificial electrical stimulation. These "side loops" are the mechanical equivalent to the loop that stores the conceptual knowledge that dogs dislike cats and that cats want to play with mice, and the word loop that completes the partial word statement "alea jacta" into "alea jacta est". It is easy to see that the dog loop links to the cat loop (or at least that the network associated with dog, etc., for the non-converted), that the cat loop links to the mouse loop, etc., the next step now is to link the 200 Hz artificial electrical stimulation to eventual lower frequency loops that are of low enough frequency that can detonate spikes on the appropriate efferent neurons that cause the known Parkinson's tremor. This is in turn important because if this theory now proposed by the inventor is correct, it immediately follows that both the fixed frequency of the dinosaur-style electrical stimulation, and the much better mixed frequency proposed by Prof. Peter Tass and collaborators can be improved with a random electrical stimulation. This is then the theoretical justification for the random electrical stimulation proposed by the inventor, but the invention is not bound to this theory be proven correct, but stands on its own. We believe that our theory will be modified and improved, so though we believe that when this simple version presented here will be enthusiastically accepted in the future, like many brilliant new theories, it will be subject to adjustments in details, while the invention will stand.

Therefore, according to our theory, Parkinson's disease is caused by an involuntary self-sustaining loops that produce low frequency circulating currents in the loop(s), with leakages to efferent neurons that continue to the hands, causing the tremor. We also postulate the existence of random isolated neuron firings which in most cases just die off, perhaps after setting a few other neurons on, but not a self-sustaining loop. If, on the other hand, there happens to be enough self-sustaining loops in some volume of the brain, then any occasional random neuron firing is liable to start a self-sustaining loop. If this occur in the vicinity of the efferent neurons that cause hand motion, and if also the damping effects of chemicals or other types are not present, or if they are present but not in enough strength, then Parkinson's tremor is set on. This self-sustaining loop can be disrupted by any higher frequency stimulation that confuses the efferent neurons, preventing them from keeping the hand tremor, as is done with currently used DBS for Parkinson's disease control. At the same time, the superposed artificially created high-frequency stimulation, say, the currently used 200 Hz, is likely to be capable, with the passage of time, to create secondary low-frequency self-sustaining loops from its own leakage current which could, in turn, easily cause the tremor, given that this 200 Hz high-frequency stimulation is exactly at the location where the offending efferent neurons are located. Moreover, if, as time passes, more and more low frequency loops are created by the artificial stimulation, and these low-frequency loops are likely to be in phase, as they are all associated with the same origin: the artificial 200 Hz stimulation. These induced, in-phase low-frequency self-sustaining loops would eventually overwhelm the artificial 200 Hz in amplitude, as they become more numerous and their combined current becomes larger and larger, this being the reason for the observed fact that often the artificial high frequency electric stimulation loses its clinical effectiveness, first requiring progressively higher stimulating voltages (which implies higher currents) then eventually becoming clinically ineffective (because the electric potential cannot be raised enough due to the battery limitations).

Supporting Arguments

We want to add the following as supporting evidence to our theory

1. The known decrease in memory recall that generally comes with old age is understandable and even expected from our model of brain working. Our model depends on the neurons that are part of each and all loops to be able to generate enough energy to replenish the losses due to electrical resistivity to the current flowing through the neurons and jumping from one to the next at the synapses. Now, it is well know that aging brings together a decrease of cellular strength, with no reason to exclude neurons from this known and visible consequence. Consequently one would expect that neurons would lose with age the capacity to generate the necessary energy to keep the loop going on, with consequent lost of memory recall, memory detail, memory association and more. The reader is recalled that the resistivity decreases the charge carriers (ions in this case), so, if the charge carriers are not replaced by other charges generated and set in motion by any of the energy sources available to the neurons, the loop is not capable of keeping the current in a steady state through it and the memory associated with it fades away.

2. Proposed experiment.

The inventor proposes an experiment that if successful would support our theory. Given that it is known that observation of a movement, or just the thought of a movement, causes neural activity at the location from where the control of the movement happens, the inventor proposes that either the intense observation of hands making steady movements, or concentrated thoughts of making the same movements, ought to cause equivalent loops to be initiated, which the inventor expects to cause at least some disruption on the Parkinson's tremor, if not its cessation altogether. While the Parkinson's tremor is the equivalent of an involuntary movement, as the heart beating is, the concentrated thought of another movement that uses similar muscles as the tremor, or the observation of another movement that uses the same muscles as the tremor, is the equivalent of a voluntary lung breathing in or breathing out—both change the involuntary movement. In the case of the thought of a process it is expected that the influence on the actual process is smaller than an actual process, so a negative result of the experiment could not be interpreted as a negation of the theory.

Description and Operation of Alternative Embodiments

In an alternative embodiment of our invention the four rings displayed on figure FIG. 1 are replaced by 16 smaller ¼ rings (approximately 80 degrees arc each), as shown in figure FIG. 4. Comparing Figures FIG. 1 and FIG. 4 it is seen that each of the four rings in FIG. 1 is split in 4 arcs separated by a small gap between each ring, which may encompass an angle of, for example 80 degrees (exemplary value only, not intended to limit the invention) for the pad and 10 degrees for the gap between any two pads part of the same idealized ring. This allows for the active region to be towards one side only of the picafina device, covering an arc of slightly less than 90 degrees (if only one quarter is used, or 180 degrees (if two quarters are used), or 270 degrees (if three quarters are used), or the full circumference (if all four quarters are used), as needed for a particular case on a particular patient, depending on the particular positioning of the picafina with respect to the area of interest. For example, if after a difficult surgery it turned out that the picafina have actually been placed on the edge of the region of interest, as shown in figure FIG. 5a and FIG. 5b, then only one or two quarter electrodes would be activated (the single electrode 4 in the case shown in FIG. 5a, two electrodes 3 and 4 in the case shown in FIG. 5b). Persons skilled in the art will note that it is possible to have more than 4 electrodes around the perimeter at a fixed distance from the endings, 4 being used as an exemplary case. For example, a large number of electrodes can be used with a much smaller number of wirings if digital addressing is used, as disclosed in other patents, and the digital addresses can be sent serially, reducing the number of address wires to just 2 (data and return), or 4 if a USB-type of serial address is used, or other small number of wires, depending on the serial protocol used for transfer. These variations for the selection of the pads are disclosed in the invention of some of the current inventors, INV1, INV2, INV3, INV4 and INV5, parts of which are copied below for completeness, but which are included in this invention in its totality.

In an alternative embodiment, shown in figure FIG. 6, our invention offers the possibility of moving the pads, or electrical stimulation points on the picafina, both translationally along its main axis (in and out of the brain) and rotationally (turning the picafina around its long axis) separately. In this alternative embodiment there are two augers (or screws), one for each motion: translation and rotation. These are shown as the screws (or augers) in supporting structures SUPP1 and SUPP2. In figure FIG. 6 the screw SC1 of SUPP1 is capable of a displacement of 1.4 mm, to match the separation between the electrodes added by a 40% engineering safety margin, but this motion is coupled to the picafina by attachment ATT1, which is only capable of pushing and pulling the picafina in and out of the brain, but not to rotate it. Therefore the rotation of the screw connected to SUPP1 is not transferred to the picafina. The screw SC2 (or auger) on supporting structure SUPP2, on the other hand, does turn the picafina. In this configuration the screw SC2 on SUPP2 may have a smaller displacement, 360 degrees, for example, which is enough to rotate the picafina to any desired angular position. Again, it is envisaged that EM2 would offer some engineering safety margin of 40%, in which case EM2 would rotate a total of 504 degrees but the invention also works without any safety margin, as well as with a rotation smaller than 360 degrees, particularly if there are several smaller arcs completing the ring-like electrode. For example, the device shown in figure FIG. 6 has four partial rings encompassing an arc of 80 degrees each, with a gap encompassing a 10 degrees angle. In such a situation the rotating screw SC2 only needs to turn 90 degrees to cover all the possible directions. Persons familiar with the art will notice that the smaller is the arc encompassed by the electrodes, the smaller is the turning required to the turning screw SC2. Such trivial variations are part of our invention.

In another alternative embodiment, herein called planarium, which is intended in applications where the area to be electrically stimulated is generally planar, the device of our invention is correspondingly of a generally planar shape, with an inner and an outer surface, being fitted with electrodes capable of delivering electric currents on one or both of its surfaces. The electrodes in this alternative embodiment may be circular in shape, or may be square or rectangular in shape, and they may be individually connected to an electrical energy source capable of delivering a voltage and current, or they may be selectable by binary addresses, which may be chosen either in parallel or in serial form, the latter form being, for example, of the general type as a USB serial port but any other serial addressing form is within the scope of the invention. Such alternative embodiment could be used, for example, on superficial brain stimulation or in TENS devices (Transcutaneous Electrical Neural Stimulation). The planarium would be similar to a deformable planar bed sheet, capable of adapting to the desirable 3-dimensional surface as a sleeping person is capable of deforming the bed sheet to conform to his shape.

Another alternative embodiment is the use of devices to move the picafina (or cordum, or TENS) that are not standard electric motors. For example, the picafina (or cordum, or TENS) may be attached to a piezoelectric crystal, which control its position. The persons skilled in the arts of technology are aware that piezoelectric crystals change dimensions with the application of electric fields (that is, voltage) to them. Piezoelectric crystals are in fact widely used in laboratories to adjust position of devices. The total reach of a piezoelectric crystal is small, but it can be built with a ratchet-type device, one that moves the device a small amount, then holds the new position with a ratchet, release the piezoelectric expansion and seat it again in the new position, then expand it again, etc. With such a ratchet Another alternative embodiment is to use a partial motor. An electric motor is composed of two parts, one which creates a magnetic field, another that suffers a force induced by the magnetic field. Energy is fed into the system by electricity which creates the magnetic field, this energy being responsible for the rotation of the motor. The part of the motor that rotates is generally known as the "rotor", while the part that creates the magnetic field is generally known as "stator". It is possible, to save space and battery energy, to have only the stator at the proximal extremity of the picafina, but not the stator. If the need arises to move the picafina, the patient would go to a physician's office, who has the necessary equipment to apply the necessary magnetic field on the rotor at the proximal end of the picafina, therefore rotating it. Looking it from a different point of view, this alternative embodiment uses an external stator. Of course that an external stator, being further away from the rotor, must create a stronger magnetic field, using more energy than the standard motor, which has a stator right around the rotor. But in this case it is a good trade, because a totally self-contained motor would have to use the battery energy, while an external stator would use an external source, say the so-called wall-plug. Such a variation has the advantage of decreasing the size and complexity of the equipment attached to the picafina, while obviating the use of battery energy to effect the motion as well.

In another alternative embodiment, herein called cordum, shown in figure FIG. 7, the stimulating device is designed to work as a heart pacemaker. Some pacemakers are attached on the outside wall of the heart, other pacemakers are attached on the inner wall of the heart. We will describe here the latter, but our invention is not limited to the position of the electrode being on the inner or outer heart surface, as it will be apparent for the practitioners of the art. Pacemakers that are attached to the inner wall of the heart are inserted into the heart from a generally neck located vein. For this alternative embodiment, the general shape of the distal end of the device is of a short screw or some other form which allows the electrode to become fixed on the heart inner wall, which is made of a non-conductive material as a plastic that is compatible with human tissues, with electrically conductive pads, or electrodes, on its surface, which are connected to an electric energy source (as a battery or a charged capacitor) by appropriate electronic circuits described below. Both the non-conductive structure and the metallic conductive pads have to be made of any of the existing art materials compatible with human tissues. As in prior art, the screw capable of being screwed onto the inner wall of the heart, often onto the inner wall of the ventricule, but can be in other parts too. Current art devices are screwed onto the inner heart wall for mechanical stability, often in the inner ventricular wall, but not necessarily so, other options being used, alone or together with a ventricular pacemaker. In our improved invention, after fixing the screw in the heart, the desired electrical stimulation is send by the connecting wires, as known by the practitioners of the art, to one or more of the electrical stimulating pads or electrodes PADi (i=1, 2, 3, . . . etc.). The choice of pads is made by trial and error by the surgeon, or later by another physician or medically trained personnel, observing on a EKG the effects of applying the electric pulses on a combination of pads. The inventors believe that the choice depends on the particular path of electrical conduction for the particular patient, and for the particular location of the stimulator, but our invention is not bound to any particular theory, but rather on the effects it produces. With pads as shown in figure FIG. 7, it is possible to apply the pacemaking electrical pulse at a precise depth onto the heart wall, as pads further down are selected, and also at any particular direction, as pads are chosen around the screw, as changing from PAD1 to PAD2, or even more, changing from PAD1 to PAD1 and PAD3 together, or even more, as changing from PAD1 to PAD3, etc. The pads that are energized (that is, the pads that are originating points for a pacemaking pulse), are selected by a digital addressing system which compares an address sent by a controlling unit to an address characteristic of each pad. The comparison is made by a standard digital circuit known as a comparator, well known in the art of digital electronics (reference_ HorowitzAndHill). When a match is found the particular pad becomes an originating point for a pacemaking pulse. To allow for more than one pad at a time, or for more than one pad at different times, said comparators are associated with a combination of pulse stretchers and latches, both being well known circuits in the art of analog and digital electronics. A possible combination may be, for example, that every time that a pad is selected, it stays selected until it is deselected by a pulse described below. Or is can be that in another possible alternative, one a pad is selected, it turns on for a particular delay time, the value of which can also be sent on the communication lines described below, all according to a pre-programmed sequence. The pad addresses and pulse delays are binary digital numbers, as used by the art of digital electronics, and the values may be sent either in parallel or in serial form. The latter may be preferred due to the difficult of passing too many wires in the cable connecting the cordum to the battery/electronics control unit, a serial communication using less wires, perhaps only two wires (bit and return or ground), or four wires (as in a USB-type serial communication), or another small number of wires, depending on the particular type of serial communication is used. This invention is not depending on any particular serial communication, which is part of the old art of digital electronics, but it depends only on the possibility of selecting particular electrode pads, which in turn select the depth and direction of insertion of the pacemaking pulse in the heart wall. The digital (parallel and serial) method is described in other pending patent of some of the authors of this patent (PPA "Method and means to address and make use of multiple electrodes for measurements and electrical stimulation of neurons and other cells including brain and heart" by Chong Il Lee and Sergio Monteiro, application No. 61/340,920 of Mar. 24, 2010, RPA "Method and means for connecting and controlling a large number of contacts for electrical cell stimulation in living organisms" by Chong Il Lee and Sergio Monteiro, application Ser. No. 12/586,763, of Sep. 28, 2009, RPA "Method and means for connecting a large number of electrodes to a measuring device" by Chong Il Lee and Sergio Monteiro, application Ser. No. 12/586,562, of Sep. 24, 2009), which are included as references in their entirety, and also copied in part in this PPA.

Saying the above in different way, alternative description, the innovation of our invention over prior art is the introduction of several relatively small points from where to originate the pacemaking pulses, in stark difference with the prior art, with which the pacemaking pulses have been introduced in the heart over the whole size of the anchoring electrode and over 360 degrees around same. The smaller originating points for the pacemaking points require the use of an addressing system to select one or a plurality of points as originating points for the pacemaking pulses, which can be made using the digital addressing system disclosed in the invention of some of us (PPA "Method and means to address and make use of multiple electrodes for measurements and electrical stimulation of neurons and other cells including brain and heart" by Chong Il Lee and Sergio Monteiro, application No. 61/340,920 of Mar. 24, 2010, RPA "Method and means for connecting and controlling a large number of contacts for electrical cell stimulation in living organisms" by Chong Il Lee and Sergio Monteiro, application Ser. No. 12/586,763, of Sep. 28, 2009, RPA "Method and means for connecting a large number of electrodes to a measuring device" by Chong Il Lee and Sergio Monteiro, application Ser. No. 12/586,562, of Sep. 24, 2009), which is included in this PPA in their entirety and partly copied as part of this application. The possibility of selecting a smaller surface area as initiating position for the pacemaking pulses allow the medical professional to introduce the pacemaking pulse in the particular depth and on the particular direction that is better suited for the correct propagation of the pacemaking pulse both in timing and phase, thereby creating a better heart beating, which is more similar to the desired one when compared with prior art pacemakers.

For the embodiment we call cordum, the rotating motion can be imparted to the tip of the device either using the same technology as used in current art, or it can be implemented by means of a rotating means at the distal extremity of the device, at or near the heart muscle, where the stimulating implant is located. Such a rotating means may be an electrical motor, but this is not necessarily so. Such a rotating means (motor or otherwise) may be also located at the proximal extremity of the cable, still within the scope of our invention. Such a rotating device can be exactly and only the existing art attachment, in which case the electrode initiation point is only based on the electrode selection, or the rotating device can be with a motor to adjust the positioning after surgery. The reader will notice that electrical stimulation waves that rotates within the body of the patient, or electrical stimulation waves that translates within the body of the patient are possible.

Nowadays most heart pacemakers are implanted from a vein, usually the sub-clavian vein, in the upper torax. The electrode is, in this case, at the end of a supporting/anchoring structure which is advanced from the insertion point in the vein until it reaches the inner part of the heart, where it is attached. The supporting structure that carries the stimulating electrode can use different technologies, one of which is a metallic screw. Such a metallic screw can then be rotated to cause it to insert itself in the inner part of the heart, from where it propagates on all 360 degrees directions out of the screw-like cordum. In the variation disclosed by our invention, the cordum is made similarly to the picafina, having a number of contacts on its surface, as seen in figures FIG. 7, FIG. 11, which are capable of delivering the stimulation at a chosen depth, determined according to the case and according to the patient needs. Also possible is to deliver the stimulation towards one direction only, the degree of directionality depending on the arc determined by each electrode. Both the directionality and the depth are known to be important factors for the pacemaker, yet to this day there exist no pacemaker capable of selecting the depth of stimulation nor the direction of stimulation. The objective of the invention is to mimic as well as possible the natural electric pulse traveling through the heart muscle, which is not nearly close achieved by existing art pacemakers.

FIGS. 8, 8a and 8b display another possible embodiment, in which the motor MOT1 is provided with a sleeve, which rides inside a slot on the support structure, which then allows the motor to move in-and-out of the brain as its axis rotates, while preventing the whole motor from rotating, that is rotating around a fixed picafina.

FIG. 8c displays other possible embodiments for adjusting the position of the electrodes, both axially (along the picafina's long dimension, or z-axis) and rotationally (along the theta or angular dimension). In this embodiment the motor is fixed and the advancement of the picafina is absorbed by a longer connecting axle CON-AXLE, which is long enough to stay in contact with the matching slot on the motor, while moting along its z-dimension.

FIG. 9 displays a solution to the problem of the relative position of the picafina with respect to the skull. The surgeon attempts to insert the picafina perpendicularly to the skull outer surface, but this is seldom accomplished perfectly, a small angle usually being necessary to adjust to the peculiar position of the area of interest, which is different from person to person, from patient to patient. In old art the picafina is cemented on a plate which is screwed on the skull, but our invention uses an intermediate motor, or motors. This necessitates the introduction of an angle adjusting wedge ANG1, which seats an angled picafina and motor on a support that may be not at 90 degrees to the picafina z-axis. The angle adjusting wedge is selected at the end of surgery, by trial and error, or measuring the angle between the picafina z-axis and the skull's locally flat surface (locally flat is here used in the mathematical sense, which is an osculating plane). In that case the picafina is first inserted in place using existing art devices and techniques, then SUPP1-SIDE (see figure FIG. 10) is screwed around it as deep as needed, then a longer measuring device (not shown) is inserted onto the hexagonal CON-AXLE, which protrudes beyond the skull, from which the angle can be measured and the appropriate angle adjusting wedge ANG1 is chosen, then the motor MOT1 is inserted in place, its distal axle matching the proximal connecting axle CON-AXLE of the picafina, then the wedge ANG1 is inserted and screwed on the motor, then finally the closing plate is screwed on the wedge ANG1 and on the skull, after which the whole device is fixed.

Note that our picafina allows for adjustment both of necessary angle of insertion of the stimulation, as shown in figure FIG. 5a and FIG. 5b, and also the necessary optimal depth of the electrode (or electrodes), to be at the center of the region of interest, as shown in figure FIG. 12a and FIG. 12b.

Conclusion, Ramifications, and Scope of Invention

Thus the reader will see that the device of my invention, whether of the picafina style (for brain), or of the cordum style (for heart), or of the TENS style (for skin), provides a highly reliable support for the electrical stimulation, in such a way that the point of electrical stimulation can be modified as needed, both along the translational and along the rotational dimensions, following a geometrical path or a random position modification, following a fixed frequency or a varying frequency or a random time between any two stimulation events and with a stimulation pulse of a fixed time length or a stimulation pulse of a random time length, and any random time being within an arbitrarily large time interval or within a limited time interval.

While my above description contains many specificities, these should not be construed as limitations on the scope of the invention, but rather as an exemplification of one preferred embodiment thereof and a few exemplary variations. Many other variations are possible. For example instead of a long, circularly shaped device, a flat support, similar to a sheet, as a deformable bed sheet capable of adjusting to most shapes while conforming to the desired 3-D surface, as the approximately cylindrical surface of an arm or the approximately spherical surface of a head or the more complex external surface of a heart can also be used for TENS stimulation on an arm, for brain cortex or for DBS stimulation, for heart stimulation, etc.

Accordingly, the scope of the invention should be determined not by the embodiment(s) illustrated, but by the appended claims and their legal equivalents.

In order to avoid obscuring the features of the present invention, the description is provided with reference to single ended implementations. The extension of the approaches to differential circuits will be apparent to one skilled in the relevant arts by reading the disclosure provided herein, and such implementations are contemplated to be covered by various aspects of the present invention.

One skilled in the relevant art, however, will readily recognize that the invention can be practiced without one or more of the specific details, or with other methods, etc. In other instances, well known structures or operations are not shown in detail to avoid obscuring the features of the invention.

SEQUENCE LISTING

Not applicable

REFERENCES

INV1: (PPA) "Method and means to address and make use of multiple electrodes for measurements and electrical stimulation of neurons and other cells including brain and heart" by Chong Il Lee and Sergio Monteiro, application No. 61/340,920 of Mar. 24, 2010, INV2: (RPA) "Method and means for connecting and controlling a large number of contacts for electrical cell stimulation in living organisms" by Chong Il Lee and Sergio Monteiro, application Ser. No. 12/586,763, of Sep. 28, 2009, INV3: (RPA) "Method and means for connecting a large number of electrodes to a measuring device" by Chong Il Lee and Sergio Monteiro, application Ser. No. 12/586, 562, of Sep. 24, 2009)

Roger Fouts "Next of Kin—What Chimpanzees Have Taught Me About Who We Are" Living Planet Book (1997)

Paul Horowitz and Winfield Hill "The Art of Electronics", $1^{st}$ and $2^{nd}$ eds, Cambridge University Press, Boston, Mass. Good for non-specialist (though technically trained) persons, that is, persons capable of think about electronic circuits, as a physicist or chemist or an electronics technician, but not necessarily EE.

D. O. Hebb "Organization of Behavior" Science Editions, NY (1949)

Eric Kandel (Kandel (2000)) gives a good overview of the current state of the art from the academic point-of-view (Robert Miller 1991) Robert Miller "Cortico hippocampal interplay and the representation of contexts in the brain" Springer (1991)

Enrico Opri, Jonathan Shute, Rene Molina, Kelly Foote, Michael Okun and Aysegul Gunduz, Closing the Loop in Deep Brain Stimulation: A Responsive Treatment for Essential Tremor (S27.005), *Neurology*, Apr. 8, 2015., and http://www.neurology.org/content/86/16_Supplement/S27.005.short Publications by Peter Tass on resynchronization therapy:

Borys Lysyansky, Olenksandr Popovych and Peter Tass "Multi-frequency activation of neuronal networks by coordinated reset stimulation" Interface Focus V.1, pg 75-85 (2011).

C. Hauptmann, Peter Tass et al. "External trial deep brain stimulation device for the application of desynchronizing stimulation techniques" J. Neural Eng. V.6, 066003 (2009).

Christian Hauptmann and Peter Tass "Restoration of segregated, physiological neuronal connectivity by desynchronizing stimulation" J. Neural Eng. V.7, 056008 (2010).

Lorenz Hoffmann, Peter Tass et al. "Modified pulse shapes for effective neural stimulation" Frontiers in Neuroeng. V. 4, article 9, (September 2011).

Borys Lysyansky, O. Popovych and Peter Tass "Optimal number of stimulation contacts for coordinated reset neuromodulation" Frontiers in Neuroeng. V. 6, article 5, (July 2013).

P. Perlikowsky, Peter Tass et al. "Periodic patterns in a ring of delay-coupled oscillators" Phys. Rev. E V. 82, n. 3, 036208 (2010).

O. Popovych, V. Krachkovskyi, Peter Tass "Phase-locking swallows in coupled oscillators with delayed feedback" Phys. Rev. E vol. 82, n. 4, 046203 (2010).

J. Pfister and Peter Tass "STDP in oscillatory recurrent networks: theoretical conditions for desynchronization and applications to deep brain stimulation" Frontiers in Comp. Neurosc., V.4, article 22 (July 2010).

Publications by May-Britt Moser and Edvard Moser on neural loops:

May-Britt Moser, "Grid cells, place cells and memory" Nobel Lecture (7 Dec. 2014).

Jonathan J. Couey, May-Britt Moser, Edvard Moser et al. "Recurrent inhibitory circuitry as a mechanism for grid formation", Nature Neuroscience V. 16, N 3, pg. 318 (March 2013).

What is claimed is:

1. A method for applying therapeutic neuromodulation by adjusting the location of an electrical stimulation caused by an electrical stimulator configured to be implanted in an animal comprising:

providing a supporting structure configured to be attached to the animal;

providing an electrode supporting structure with a proximal extremity, a distal extremity, a surface and an inner volume;

providing a plurality of pads or electrodes at the surface of the electrode supporting structure;

providing one or more electronic controlling unit which is configured to change the state of some of the electrodes from on to off and/or from off to on at different times or to leave the state of some of the electrodes unchanged;

providing electrically connecting means connecting the electrodes at the surface of the electrode supporting structure to the one or more electronic controlling unit wherein, the one or more electronic controlling unit is configured for providing a change in the electrodes that are turned on providing electrical stimulation, wherein the locus of the electrical stimulation occurred at precise locations along the electrode supporting structure wherein it is possible to apply the electrical stimulation at a a precise depth and at a precise angular orientation with respect to the target tissue, Wherein the electrical stimulation locus transition from either a single electrode or a combination of electrodes to either a different electrode or combination of electrodes in a pre-determined pattern.

2. The method of claim 1 wherein the location changes of the stimulation locus cause a moving propagating stimulation through the target tissue of the animal.

3. The method of claim 1 wherein the change in the position of application of the electrical stimulation is a comprehensive random sequence.

4. The method of claim 1 wherein the time elapsed between the initiation of the electrical stimulation from one electrode to another electrode is a comprehensive random time sequence.

5. The method of claim 4 wherein the time elapsed between the initiation of the electrical stimulation from one electrode to another electrode is a comprehensive random time sequence that assumes values within a minimum time value and a maximum time value.

6. The method of claim 1 wherein the duration of the electrical stimulation forms a comprehensive random time sequence.

7. The method of claim 6 wherein the duration of the electrical stimulation forms a comprehensive random time sequence that assumes values within a minimum time value and a maximum time value.

8. The method of claim 1 wherein the change in the stimulating electrodes provides a rotating electrical stimulation wherein the most recently connected electrodes at the "on" state at the surface of the electrode supporting structure and the last disconnected electrodes at the "off" state behind, describe a rotation with respect to the intended target tissue of the animal.

9. The method of claim 1 wherein the change in the stimulating electrodes provides a translating electrical stimulation created by the advancing along the electrode supporting structure of the electrodes at the "on" state and the electrodes at the "off" states behind the "on" state.

10. An electrical stimulation apparatus for applying therapeutic neuromodulation by adjusting the location of an electrical stimulation caused by an electrical stimulator configured to be implanted in an animal comprising:
   providing a supporting structure configured to be attached to the animal,
   providing an electrode supporting structure with a proximal extremity, a distal extremity, a surface and an inner volume;
   providing a plurality of pads or electrodes at the surface of the electrode supporting structure,
   providing one or more electronic controlling unit which is configured to change the state of some of the electrodes from on to off and/or from off to on at different times or to leave the state of some of the electrodes unchanged,
   providing electrically connecting means connecting the electrodes at the surface of the electrode supporting structure to the one or more electronic controlling unit wherein,
   the one or more electronic controlling unit is configured for providing a change in the electrodes that are turned on providing electrical stimulation,
   wherein the locus of the electrical stimulation occurred at precise locations along the electrode supporting structure wherein it is possible to apply the electrical stimulation at a precise depth and at a precise angular orientation with respect to the targed tissue,
   wherein the electrical stimulation locus transition from either a single electrode or a combination of electrodes to either a different electrode or combination of electrodes in a pre-determined pattern.

11. The electrical stimulation apparatus of claim 10 wherein the location changes of the stimulation locus cause a moving propagating stimulation through the target tissue of the animal.

12. The electrical stimulation apparatus of claim 11 wherein the location changes of the stimulation locus cause a moving propagating stimulation through the target tissue of the animal such that the locus of the electrical stimulation moves either on a translating pattern or on a rotating pattern with respect to the electrode supporting structure.

13. The electrical stimulation apparatus of claim 10 wherein the change in the position of the electrical stimulation is a comprehensive random sequence.

* * * * *